United States Patent
Lim et al.

(10) Patent No.: US 8,986,855 B2
(45) Date of Patent: Mar. 24, 2015

(54) HETEROCYCLIC COMPOUND AND ORGANIC LIGHT-EMITTING DEVICE INCLUDING THE SAME

(75) Inventors: Jin-O Lim, Yongin (KR); Seok-Hwan Hwang, Yongin (KR); Young-Kook Kim, Yongin (KR); Hye-Jin Jung, Yongin (KR); Sang-Hyun Han, Yongin (KR); Bo-Ra Lee, Yongin (KR); Jong-Hyuk Lee, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 442 days.

(21) Appl. No.: 13/396,859

(22) Filed: Feb. 15, 2012

(65) Prior Publication Data

US 2013/0001529 A1    Jan. 3, 2013

(30) Foreign Application Priority Data

Jun. 29, 2011 (KR) .................. 10-2011-0064077

(51) Int. Cl.

| | | |
|---|---|---|
| H01L 51/54 | (2006.01) | |
| C09K 11/06 | (2006.01) | |
| C07D 401/14 | (2006.01) | |
| C07D 221/18 | (2006.01) | |
| C07D 401/12 | (2006.01) | |
| C07D 401/10 | (2006.01) | |
| H01L 51/00 | (2006.01) | |
| H01L 51/50 | (2006.01) | |

(52) U.S. Cl.
CPC ............ *C07D 401/12* (2013.01); *C07D 401/14* (2013.01); *C07D 221/18* (2013.01); *C07D 401/10* (2013.01); *H01L 51/0061* (2013.01); *H01L 51/0067* (2013.01); *H01L 51/0072* (2013.01); *H01L 51/5072* (2013.01); *Y10S 428/917* (2013.01)
USPC ...... 428/690; 428/917; 257/40; 257/E51.024; 546/42; 544/180

(58) Field of Classification Search
None
See application file for complete search history.

(56) References Cited

U.S. PATENT DOCUMENTS

| | | | |
|---|---|---|---|
| 5,635,308 | A | 6/1997 | Inoue et al. |
| 5,645,948 | A | 7/1997 | Shi et al. |
| 5,972,247 | A | 10/1999 | Shi et al. |
| 6,465,115 | B2 | 10/2002 | Shi et al. |
| 6,596,415 | B2 | 7/2003 | Shi et al. |
| 7,768,191 | B2 | 8/2010 | Boerner et al. |
| 2007/0167654 | A1 | 7/2007 | Yabunouchi et al. |
| 2007/0191587 | A1 | 8/2007 | Kanitz et al. |
| 2009/0149649 | A1 | 6/2009 | Shin et al. |

FOREIGN PATENT DOCUMENTS

| | | |
|---|---|---|
| JP | 8-12600 A | 1/1996 |
| JP | 2000-003782 A | 1/2000 |
| KR | 10-2006-0082668 A | 7/2006 |
| KR | 10-2006-0127101 A | 12/2006 |
| KR | 10-2007-0110526 A | 11/2007 |
| KR | 10-2008-0083148 A | 9/2008 |
| KR | 10-2009-0059849 A | 6/2009 |

OTHER PUBLICATIONS

Randic et al. J. Am. Chem. Soc. 1985, 107, 849-859. Year of publication: 1985.*
Buu-Hoi et al. J. Chem. Soc., Perkin Trans. 1, 1972, 263-265. Year of publication: 1972.*
Appl. Phys. Lett. 51, Sep. 21, 1987: Organic electroluminescent diodes( Received May 12, 1987, accepted for publication Jul. 20, 1987); C.W. Tang and S.A. Vanslyke.
Appl. Phys. Lett. 57 (6) Aug. 6, 1990: Confinement of charge carriers and molecular excitons within 5-nm-thick emitter layer in organic electroluminescent devices with a double heterostructure (Received Jan. 29, 1990, accepted May 30, 1990) by Chihaya Adachi et al.
J. Am. Chem. Soc. 2000, 122, 1832-1833: Synthesis, Characterization, and Electron-Transport Property of Perfluorinated Phenylene Dendrimers by Youichi Sakamoto et al. (Received Nov. 22, 1999).
Chemistry Letters 2001: Diphenylamono-Substituted 2,5-Diarylsiloles for Single-Layer Organic Electroluminescent Devices (Received Nov. 10, 2000) by Shigehiro Yamaguchi et al.
Chinese Office Action dated Jan. 27, 2015 of the corresponding CN Patent Application No. 201211085177.7. "Request for Entry" attached.
"Syntheses Dans le Domaine des Composes Polycycliques AROMATIQUES_XXIII", F. Geerts-Evrard et al. Tetrahedron, Supplement No. 7. pp. 287-294. Dec. 31, 1966. Cited in Chinese Office Action dated Jan. 27, 2015 of the corresponding CN Patent Application No. 201211085177.7. English abstract is on p. 1.

\* cited by examiner

*Primary Examiner* — Andrew K Bohaty
(74) *Attorney, Agent, or Firm* — Robert E. Bushnell, Esq.

(57) ABSTRACT

Derivatives of benzo[h]naphtho[1,2-f]quinoline and organic light emitting devices (OLEDs) including them are disclosed. The subject compounds impart high efficiency, low driving voltage, high luminance and long lifespan to the OLEDs. The subject compounds may be used as light emitting materials, as electron transporting materials, or as electron injecting materials. Because the subject compounds have high glass transition temperatures or high melting points, OLEDs including them exhibit high durability in storage or operation. Suitable substituents may be selected from deuterium, alkyl, alkenyl, alkynyl, cycloalkyl, alkoxy, aryloxy, arylthio, aryl, aryl- or heteroaryl-substituted amino, heteroaryl, condensed polycyclic, halogen, cyano, nitro, hydroxyl and carboxyl groups.

19 Claims, 1 Drawing Sheet

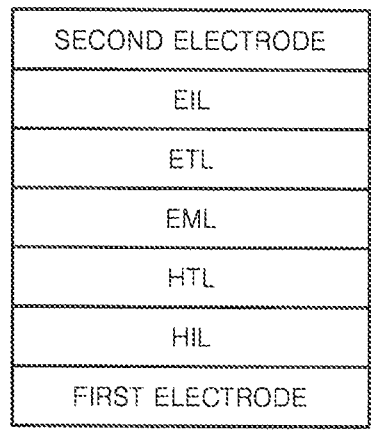

HETEROCYCLIC COMPOUND AND ORGANIC LIGHT-EMITTING DEVICE INCLUDING THE SAME

CROSS-REFERENCE TO RELATED PATENT APPLICATION

This application claims the benefit of Korean Patent Application No. 10-2011-0064077, filed on Jun. 29, 2011 (in the Korean Intellectual Property Office, the disclosure of which is incorporated herein by reference.

BACKGROUND OF THE INVENTION

1. Field of the Invention

The present invention relates to a heterocyclic compound represented by Formula 1 and an organic light-emitting device including the heterocyclic compound.

2. Description of the Related Art

Light-emitting devices are self-emission type display devices and have a wide viewing angle, a high contrast ratio, and a short response time. Due to these characteristics, light-emitting devices are drawing more attention. Such light-emitting devices can be roughly classified into inorganic light-emitting devices that include emission layers containing inorganic compounds, and organic light-emitting devices that include emission layers containing organic compounds. Specifically, organic light-emitting devices have higher luminance, lower driving voltages, and shorter response times than inorganic light-emitting devices, and can render multi-colored displays. Thus, much research into such organic light-emitting devices has been conducted. Typically, an organic light-emitting device has a stack structure including an anode, a cathode and an organic emission layer interposed therebetween. However, a hole injection layer and/or a hole transport layer may be further stacked between the anode and the organic emission layer, and/or an electron transport layer may be further stacked between the organic emission layer and the cathode. In other words, an organic light-emitting device may have a stack structure of anode/hole transport layer/organic emission layer/cathode or a stack structure of anode/hole transport layer/organic emission layer/electron transport layer/cathode.

As a material for forming the organic emission layer, naphthalene derivatives can be used. However, organic light-emitting devices including such materials may not have satisfactory life span, efficiency, and power consumption characteristics, thereby improvement in this regard still being necessary.

SUMMARY OF THE INVENTION

The present invention provides a heterocyclic compound having improved electrical characteristics, charge transporting capabilities and light-emission capabilities.

The present invention provides an organic light-emitting device including the heterocyclic compound.

The present invention provides a flat panel display device including the organic light-emitting device.

According to an aspect of the present invention, there is provided a heterocyclic compound represented by Formula 1 below:

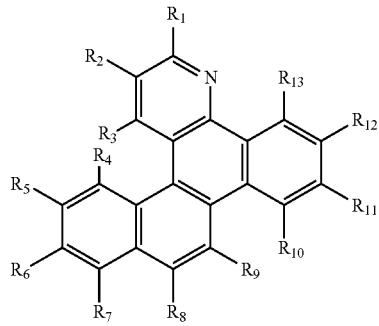

Formula 1 wherein, in Formula 1, $R_1$ to $R_{13}$ may be each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ aryl group, an amino group substituted with a $C_6$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group; and $R_1$ and $R_2$ may be optionally linked to form an aromatic ring.

$R_1$, $R_2$, and $R_8$ in Formula 1 may be each independently a substituted or unsubstituted $C_6$-$C_{20}$ aryl group, a substituted or unsubstituted $C_3$-$C_{20}$ heteroaryl group, or a substituted or unsubstituted $C_5$-$C_{20}$ condensed polycyclic group.

$R_3$ to $R_7$, and $R_9$ to $R_{13}$ in Formula 1 may be each independently a hydrogen atom or a deuterium atom.

$R_1$ and $R_2$ in Formula 1 may be each independently selected from the group consisting of a hydrogen atom, a deuterium atom, a halogen atom, a cyano group, a substituted or unsubstituted $C_1$-$C_{20}$ alkyl group, and groups represented by Formulae 2a to 2e below:

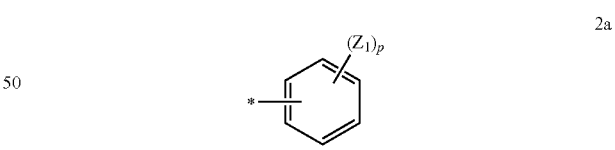

2a

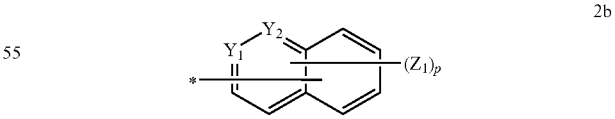

2b

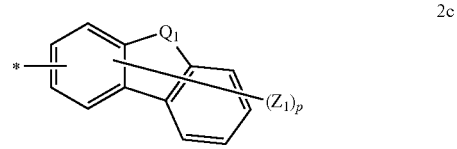

2c

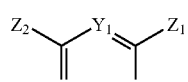
2d

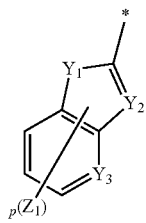
2e wherein, in Formulae 2a to 2e, $Q_1$ may be a linking group represented by —C($R_{14}$)($R_{15}$)—, —N($R_{16}$)—, —S—, or —O—; $Y_1$, $Y_2$, and $Y_3$ may be each independently a linking group represented by —N═, —N($R_{17}$)—, or —C($R_{18}$)═; $Z_1$, $Z_2$, $R_{14}$, $R_{15}$, $R_{16}$, $R_{17}$, and $R_{18}$ may be each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p may be an integer from 1 to 7; and * indicates a binding site.

$R_8$ in Formula 1 may be one of the groups represented by Formulae 3a to 3j below:

3a

3b

3c

3d

3e

3f

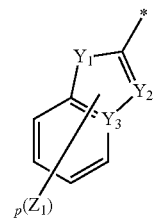

3g

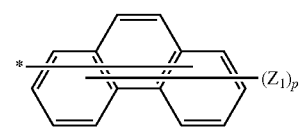

3h

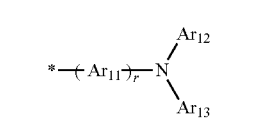

3i

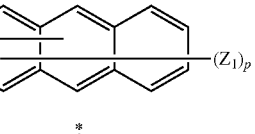

3j

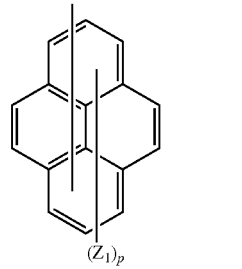

wherein, in Formulae 3a to 3j, $Q_1$ may be a linking group represented by —C($R_{14}$)($R_{15}$)—, —N($R_{16}$)—, —S—, or —O—; $Y_1$, $Y_2$, and $Y_3$ may be each independently a linking group represented by —O—, —N═, —N($R_{17}$)—, or —C($R_{18}$)═; $Z_1$, $Z_2$, $Ar_{12}$, $Ar_{13}$, $R_{14}$, $R_{15}$, $R_{16}$, $R_{17}$, and $R_{18}$ may be each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; $Ar_{11}$ may be a substituted or unsubstituted $C_1$-$C_{20}$ alkylene group, a substituted or unsubstituted $C_6$-$C_{20}$ arylene group, or a substituted or unsubstituted $C_3$-$C_{20}$ heteroarylene group; p may be an integer from 1 to 9; r may be an integer from 0 to 5; and

* indicates a binding site.

$R_1$ and $R_2$ in Formula 1 may be each independently selected from the group consisting of a hydrogen atom, a deuterium atom, and groups represented by Formulae 4a to 4g below, or may be linked to form a benzene ring:

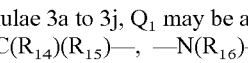

4a

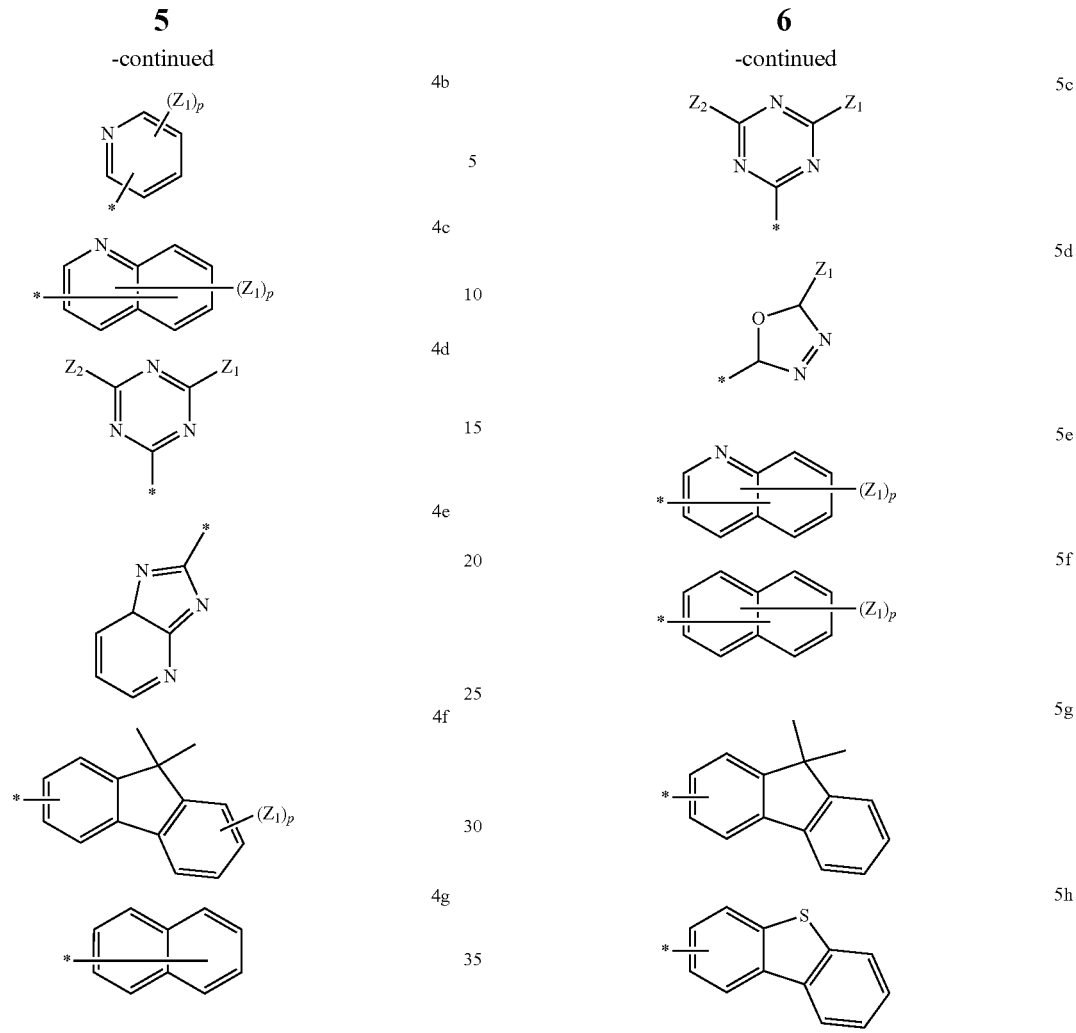

wherein, in Formulae 4a to 4g, $Z_1$ and $Z_2$ may be each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p may be an integer from 1 to 6; and * indicates a binding site.

$R_8$ in Formula 1 may be one of the groups represented by Formulae 5a to 5o below:

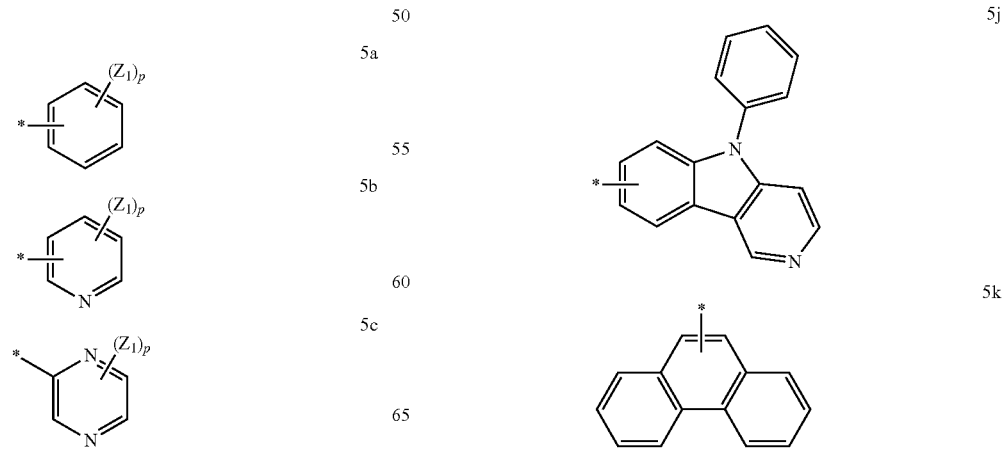

5l

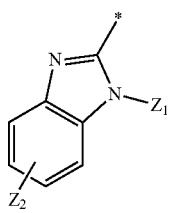

5m

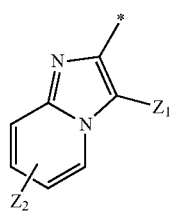

5n

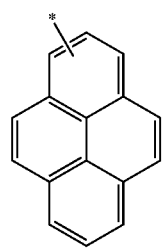

5o

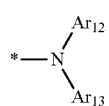

wherein, in Formulae 5a to 5o, $Z_1$, $Z_2$, $Ar_{12}$, and $Ar_{13}$ may be each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p may be an integer from 1 to 7; and * indicates a binding site.

The compound of Formula 1 may include one of the compounds below:

3

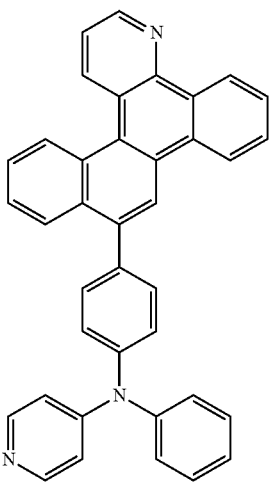

8

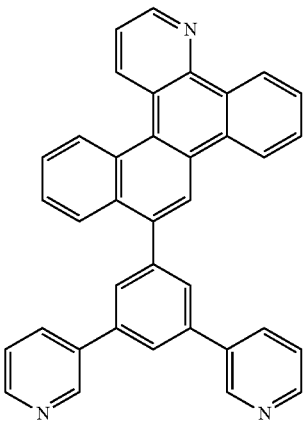

18

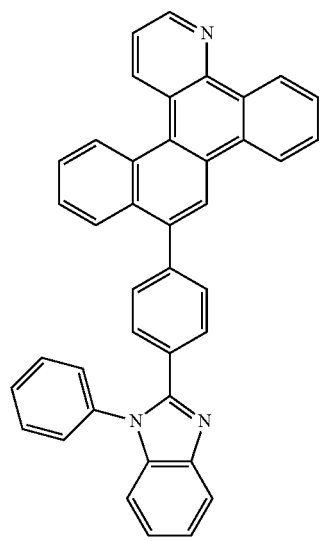

37

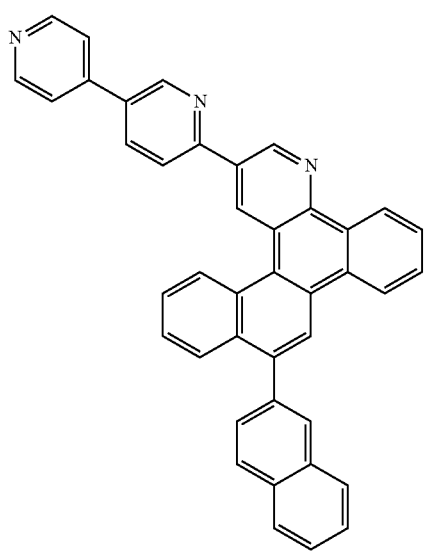

-continued

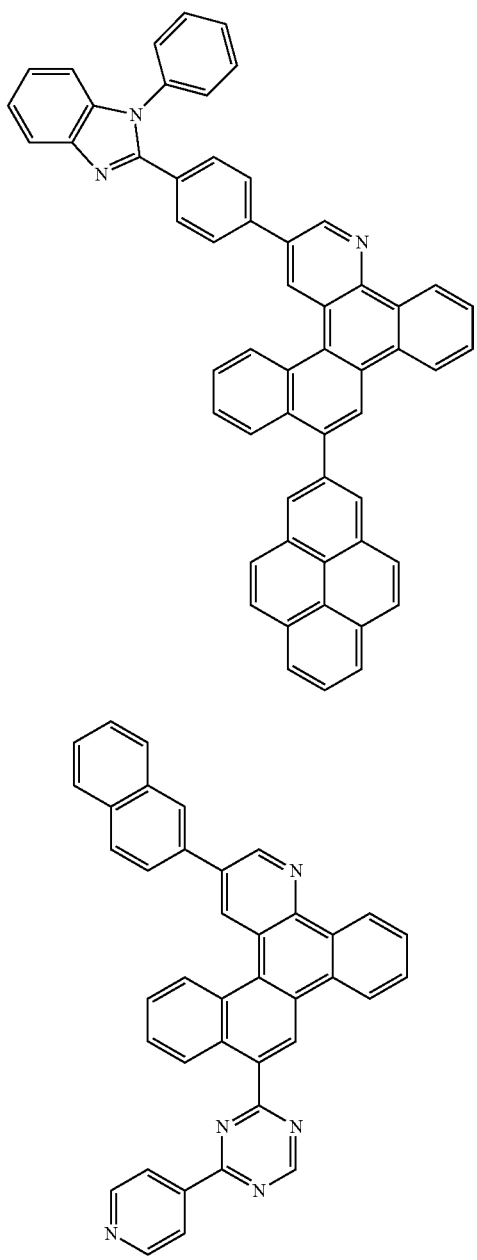

According to another aspect of the present invention, there is provided an organic light-emitting device including: a first electrode; a second electrode; and an organic layer between the first electrode and the second electrode, the organic layer comprising a first layer including the above-described heterocyclic compound.

The first layer may include at least one layer selected from the group consisting of a hole injection layer, a hole transport layer, a functional layer having both hole injection and hole transport capabilities, an emission layer, an electron injection layer, an electron transport layer, and a functional layer having both electron injection and electron transport capabilities.

The first layer may include at least one layer selected from the group consisting of a hole injection layer, a hole transport layer, a functional layer having both hole injection and hole transport capabilities, an emission layer, an electron injection layer, an electron transport layer, and a functional layer having both electron injection and electron transport capabilities, and the first layer further include a charge generating material.

The organic layer may further include a hole injection layer, a hole transport layer, a functional layer having both hole injection and hole transport capabilities, an emission layer, a hole blocking layer, an electron transport layer, an electron injection layer, or a combination of at least two thereof.

At least one of the hole injection layer, the hole transport layer, and the functional layer having hole injection and hole transport capabilities may further include a charge generating material.

The emission layer may include a host and a dopant, the dopant including a fluorescent dopant or a phosphorescent dopant.

The phosphorescent dopant may include an organometallic complex including at least one selected from the group consisting of iridium (Ir), platinum (Pt), osmium (Os), rhenium (Re), titanium (Ti), zirconium (Zr), hafnium (Hf), and a combination of at least two thereof.

The electron transport layer may include an electron transporting organic material and a metal-containing material.

The metal-containing material may include a lithium (Li) complex.

The first layer including the heterocyclic compound of Formula 1 may be formed using a wet process.

According to another aspect of the present invention, there is provided a flat panel display device including the above-described organic light-emitting device, wherein the first electrode of the organic light-emitting device may be electrically connected to a source electrode or a drain electrode of a thin-film transistor.

BRIEF DESCRIPTION OF THE DRAWING

The above and other features and advantages of the present invention will become more apparent by describing in detail exemplary embodiments thereof with reference to the attached drawing in which:

FIG. 1 illustrates the structure of an organic light-emitting device according to an embodiment of the present invention.

DETAILED DESCRIPTION OF THE INVENTION

Anthracene derivatives are widely known as materials for an organic emission layer. For example, an organic light-emitting device manufactured using a compound of phenylanthracene dimer or trimer is widely known. However, such organic light-emitting devices have a narrow energy gap and lower blue-light color purity since two or three oligomeric species of anthracene are linked by conjugation.

In addition, such compounds are highly vulnerable to oxidation and thus are liable to produce impurities, necessitating purification. In order to overcome these drawbacks, organic light-emitting devices manufactured using an anthracene compound having naphthalene groups at 1,9 positions of anthracene or using a diphenylanthracene compound including an aryl group at m-position of the phenyl group have been introduced. However, these organic light-emitting devices have a lower light-emission efficiency.

Organic light-emitting devices may also be manufactured using nathphalene-substituted monoanthracene derivatives. However, the light-emission efficiency thereof is low (about 1 cd/A), and thus such organic light-emitting devices are not suitable for practical use. Furthermore, organic light-emitting devices may be manufactured using phenylanthracene compounds including aryl substituents at m-position. Such a compound has excellent thermal resistance but leads to an unsatisfactorily low light-emission efficiency of about 2 cd/A.

The present invention will now be described more fully with reference to the accompanying drawings, in which exemplary embodiments of the invention are shown.

An aspect of the present invention provides a heterocyclic compound represented by Formula 1 below.

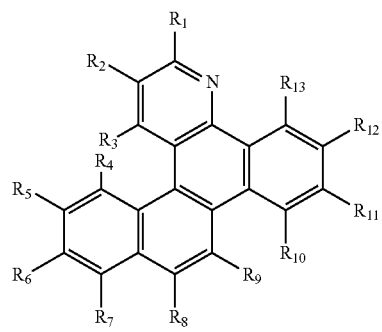

Formula 1

In Formula 1, $R_1$ to $R_{13}$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ aryl group, an amino group substituted with a $C_6$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group. Optionally, $R_1$ and $R_2$ may be linked to form an aromatic ring.

In some embodiments the heterocyclic compound of Formula 1 may be used as a light-emitting material, an electron-transporting material or an electron-injecting material. The heterocyclic compound of Formula 1 having a heterocyclic group in the molecules thereof has a high glass transition temperature (Tg) or a high melting point due to the inclusion of the heterocyclic group. Thus, the heterocyclic compound has high heat resistance against Joule's heat generated in an organic layer, between organic layers, or between an organic layer and a metal electrode when light emission occurs, and has high durability in high-temperature environments.

An organic light-emitting device manufactured using the heterocyclic compound of Formula 1 has high durability when stored or operated.

Substituents in the heterocyclic compound of Formula 1 will now be described in detail.

In some embodiments, $R_1$, $R_2$, and $R_8$ in Formula 1 above may be each independently a substituted or unsubstituted $C_6$-$C_{20}$ aryl group, or a substituted or unsubstituted $C_3$-$C_{20}$ heteroaryl group, or a substituted or unsubstituted $C_5$-$C_{20}$ condensed polycyclic group.

In some embodiments, $R_3$ to $R_7$ and $R_9$ to $R_{13}$ in Formula 1 are each independently a hydrogen atom or a deuterium atom.

In some embodiments $R_1$ and $R_2$ in Formula 1 may be each independently a hydrogen atom, a deuterium atom, a halogen atom, a cyano group, a substituted or unsubstituted $C_1$-$C_{20}$ alkyl group, or groups represented by Formulae 2a to 2e below:

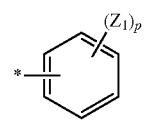

2a

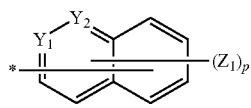

2b

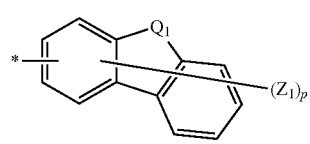

2c

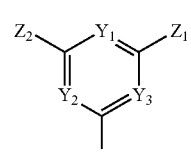

2d

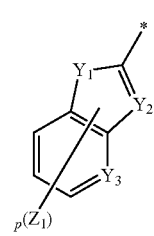

2e

In Formulae 2a to 2e, $Q_1$ is a linking group represented by —C($R_{14}$)($R_{15}$)—, —N($R_{16}$)—, —S—, or —O—; $Y_1$, $Y_2$ and $Y_3$ are each independently a linking group represented by —N═, —N($R_{17}$)—, or —C($R_{18}$)═; and $Z_1$, $Z_2$, $R_{14}$, $R_{15}$, $R_{16}$, $R_{17}$, and $R_{18}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 7; and * indicates a binding site.

In some embodiments $R_8$ in Formula 1 is one of the groups represented by Formulae 3a to 3j below:

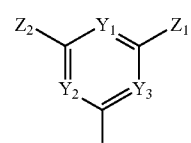

3a

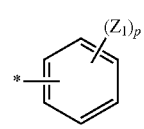

3b

-continued

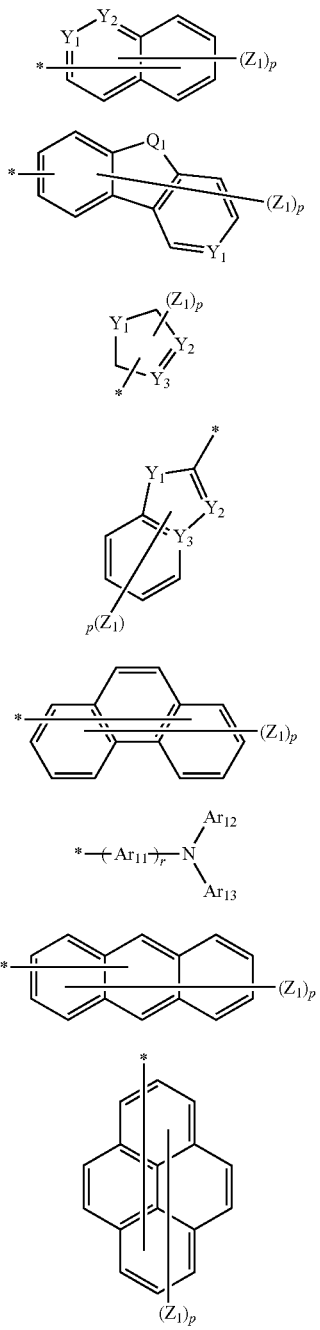

In Formulae 3a to 3j, $Q_1$ is a linking group represented by —$C(R_{14})(R_{15})$—, —$N(R_{16})$—, —S—, or —O—; $Y_1, Y_2$, and $Y_3$ are each independently a linking group represented by —O—, —N=, —$N(R_{17})$—, or —$C(R_{18})$=; $Z_1, Z_2, Ar_{12}, Ar_{13}, R_{14}, R_{15}, R_{16}, R_{17}$, and $R_{18}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; $Ar_{11}$ is a substituted or unsubstituted $C_1$-$C_{20}$ alkylene group, a substituted or unsubstituted $C_6$-$C_{20}$ arylene group, or a substituted or unsubstituted $C_3$-$C_{20}$ heteroarylene group; p is an integer from 1 to 9; r is an integer from 0 to 5; and * indicates a binding site.

In some embodiments, $R_1$ and $R_2$ in Formula 1 are each independently selected from the group consisting of a hydrogen atom, a deuterium atom, and groups represented by Formulae 4a to 4g below, or are linked to form a benzene ring:

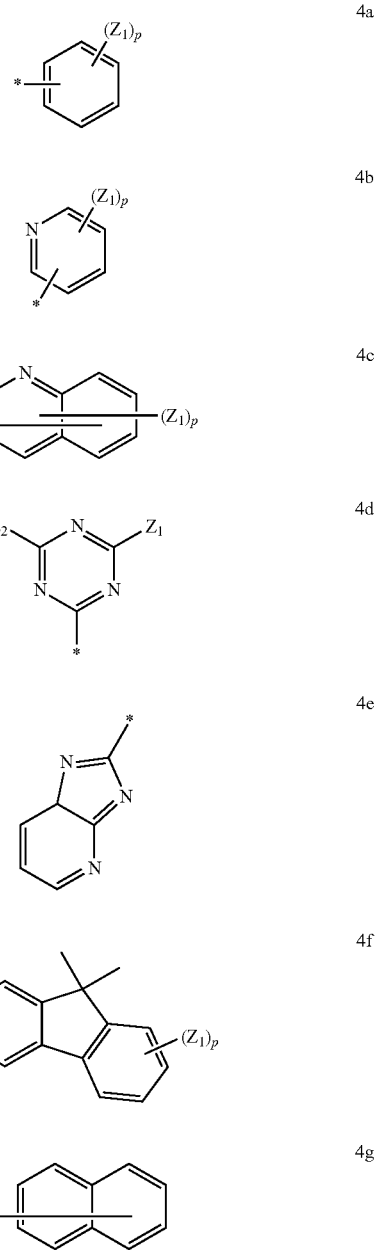

In Formulae 4a to 4g, $Z_1$ and $Z_2$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 6; and * indicates a binding site.

In some embodiments $R_8$ in Formula 1 is one of the groups represented by Formulae 5a to 5o below:

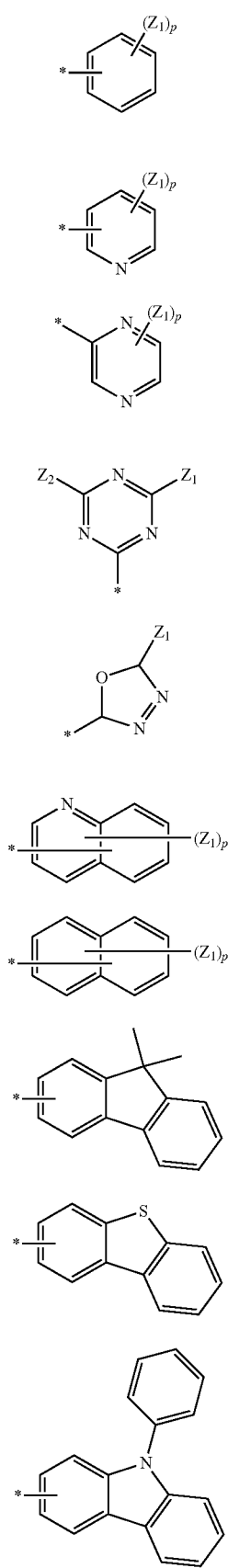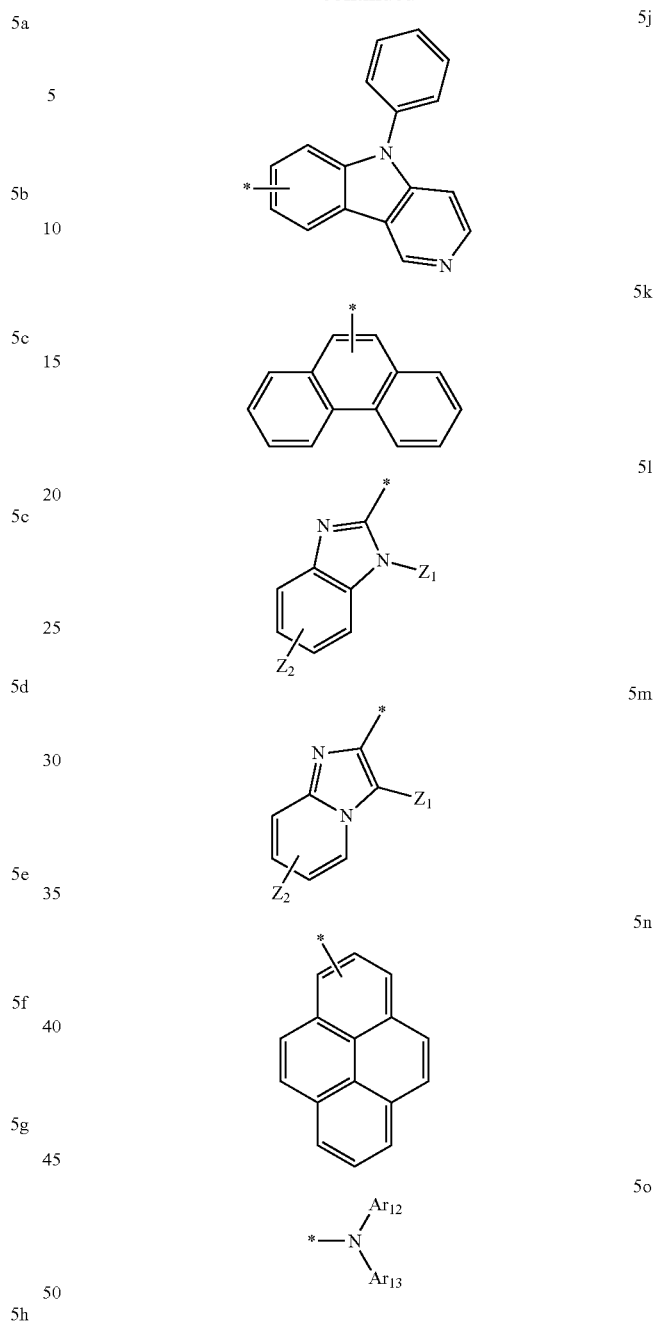

In Formulae 5a to 5o, $Z_1$, $Z_2$, $Ar_{12}$, and $Ar_{13}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 7; and * indicates a binding site.

Hereinafter, substituents described in conjunction with the above formulae will now be described in detail. In this regard, the numbers of carbons in substituents are presented only for illustrative purposes and do not limit the characteristics of the substituents The unsubstituted $C_1$-$C_{60}$ alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group indicates an unsaturated alkyl groups having at least one carbon-carbon double bond in the center or at a terminal of the alkyl group. Examples of the alkenyl group include an ethenyl group, a propenyl group, a butenyl group, and the like. At least one hydrogen atom in the unsubstituted alkenyl group may be substituted with a substituent described above in conjunction with the alkyl group.

The unsubstituted $C_2$-$C_{60}$ alkynyl group indicates an alkyl group having at least one carbon-carbon triple bond in the center or at a terminal of the alkyl group. Examples of the unsubstituted $C_2$-$C_{20}$ alkynyl group include acetylene, propylene, phenylacetylene, naphthylacetylene, isopropylacetylene, t-butylacetylene, diphenylacetylene, and the like. At least one hydrogen atom in the alkynyl group may be substituted with a substituent described above in conjunction with the alkyl group.

The unsubstituted $C_3$-$C_{60}$ cycloalkyl group indicates a $C_3$-$C_{60}$ cyclic alkyl group wherein at least one hydrogen atom in the cycloalkyl group may be substituted with a substituent described above in conduction with the $C_1$-$C_{60}$ alkyl group.

The unsubstituted $C_1$-$C_{60}$ alkoxy group indicates a group having a structure of —OA wherein A is an unsubstituted $C_1$-$C_{60}$ alkyl group as described above. Non-limiting examples of the unsubstituted $C_1$-$C_{60}$ alkoxy group include a methoxy group, an ethoxy group, a propoxy group, an iso-propyloxy group, a butoxy group, and a pentoxy group. At least one hydrogen atom of the alkoxy group may be substituted with a substituent such as those described above in conjunction with the alkyl group.

The unsubstituted $C_6$-$C_{60}$ aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted $C_1$-$C_{60}$ alkyl group.

Examples of the substituted or unsubstituted $C_6$-$C_{60}$ aryl group include, but are not limited to, a phenyl group, a $C_1$-$C_{10}$ alkylphenyl group (for example, ethylphenyl group), a halophenyl group (for example, o-, m-, and p-fluorophenyl group, dichlorophenyl group), a cyanophenyl group, dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, a o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_3$-$C_{60}$ heteroaryl group used herein includes one, two or three hetero atoms selected from N, O, P and S. At least two rings may be fused to each other or linked to each other by a single bond. Examples of the unsubstituted $C_4$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted $C_1$-$C_{60}$ alkyl group.

The unsubstituted $C_6$-$C_{60}$ aryloxy group is a group represented by —$OA_1$ wherein $A_1$ may be a $C_6$-$C_{60}$ aryl group. An example of the aryloxy group is a phenoxy group. At least one hydrogen atom in the aryloxy group may be substituted with a substituent described above in conjunction with the unsubstituted $C_1$-$C_{60}$ alkyl group.

The unsubstituted $C_6$-$C_{60}$ arylthio group is represented by —$SA_1$ where $A_1$ may be a $C_6$-$C_{60}$ aryl group. Non-limiting examples of the arylthio group include a benzenethio group and a naphthylthio group. At least one hydrogen atom in the arylthio group may be substituted with a substituent described above in conjunction with the unsubstituted $C_1$-$C_{60}$ alkyl group.

The unsubstituted $C_5$-$C_{60}$ arylthio group is represented by —$SA_1$ where $A_1$ may be a $C_5$-$C_{60}$ aryl group. Non-limiting examples of the arylthio group include a benzenethio group and a naphthylthio group. At least one hydrogen atom in the arylthio group may be substituted with a substituent described above in conjunction with the unsubstituted $C_1$-$C_{60}$ alkyl group.

The unsubstituted $C_6$-$C_{60}$ condensed polycyclic group used herein refers to a substituent including at least two rings wherein at least one aromatic ring and/or at least one non-aromatic ring are fused to each other, or refers to a substitutent having an unsaturated group in a ring that may not form a conjugate structure. The unsubstituted $C_6$-$C_{60}$ condensed polycyclic group is distinct from an aryl group or a heteroaryl group in terms of being non-aromatic.

Examples of the heterocyclic compound represented by Formula 1 may include Compounds 1 to 65 represented by the following formulae. However, the heterocyclic compound of Formula 1 is not limited thereto.

-continued

| 1 | 4 |
| 2 | 5 |
| 3 | 6 |

7
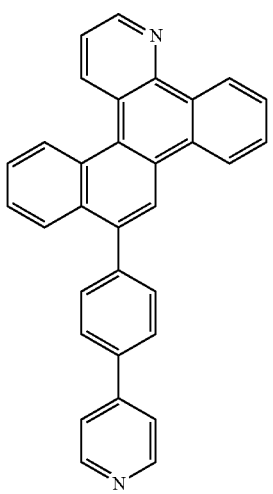
8
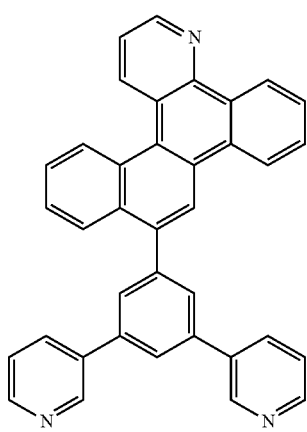
9
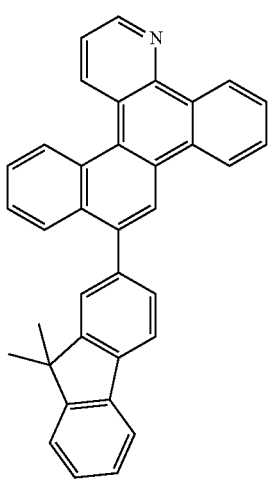
10
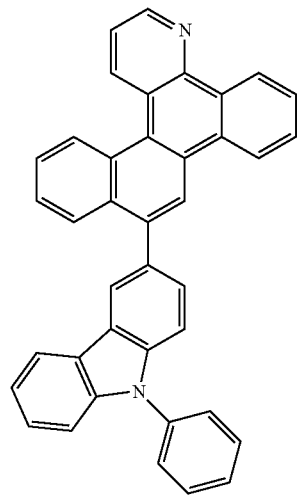
11
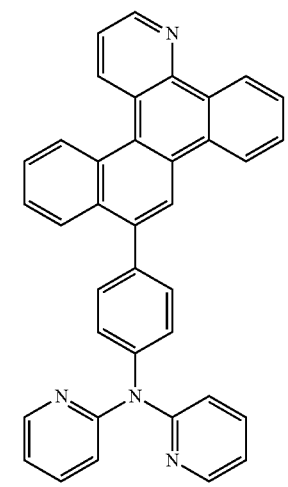
12
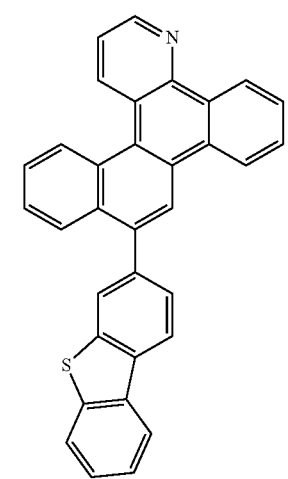

13
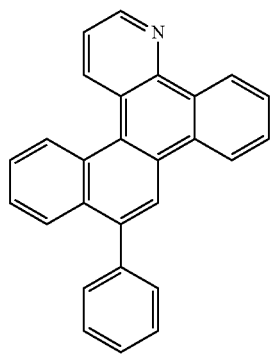
14
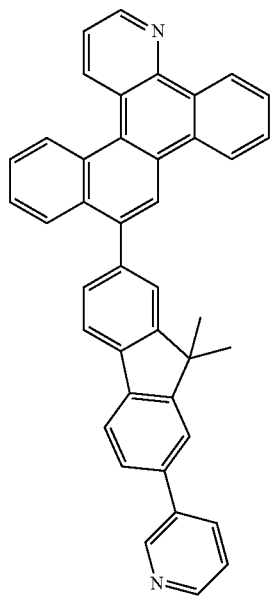
15
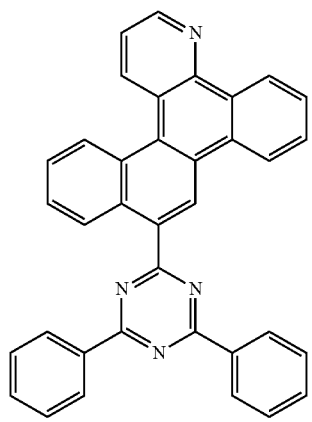
16
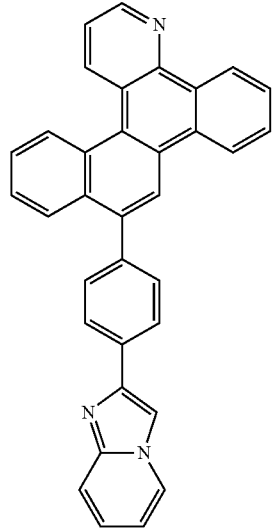
17
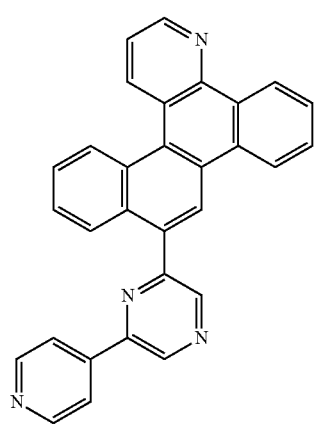
18
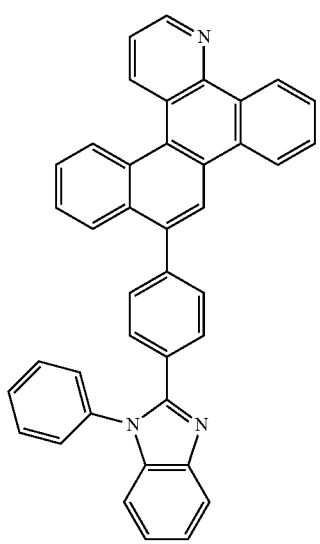

19
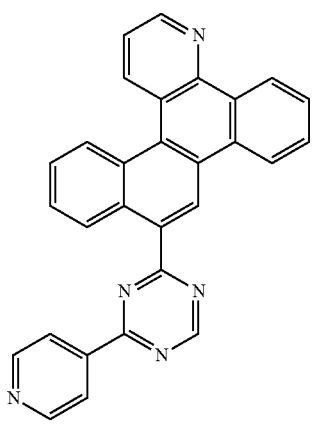
20
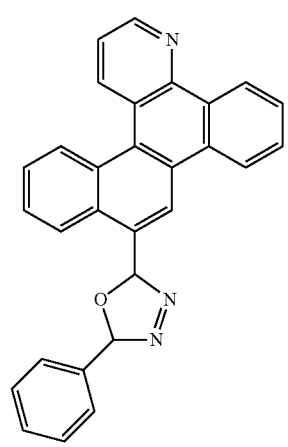
21
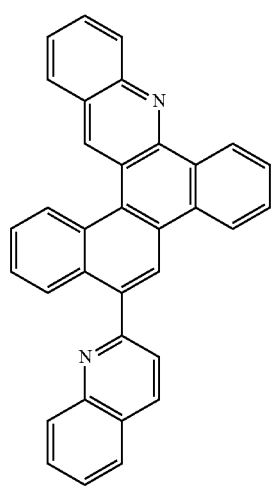
22
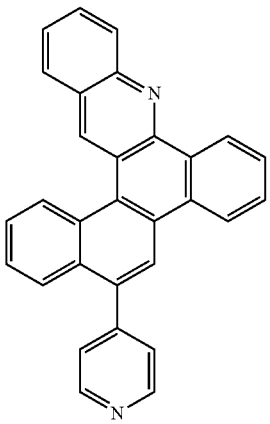
23
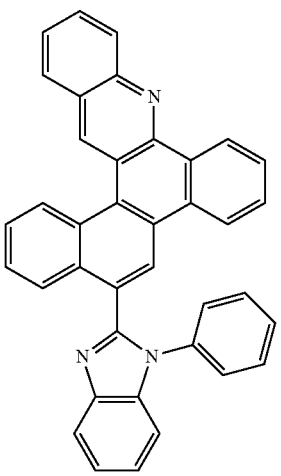
24
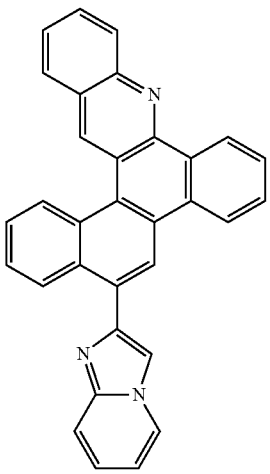

-continued
25
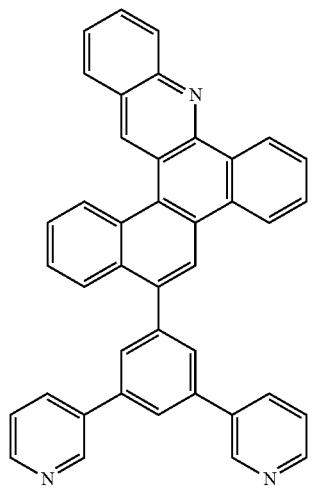
26
28
-continued
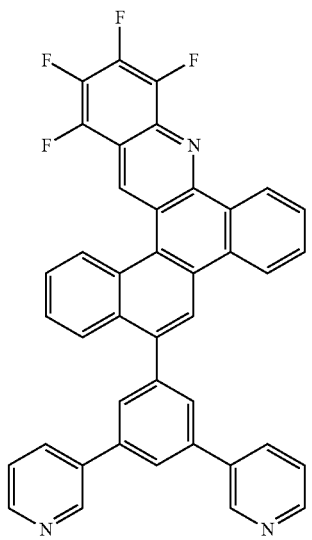
29
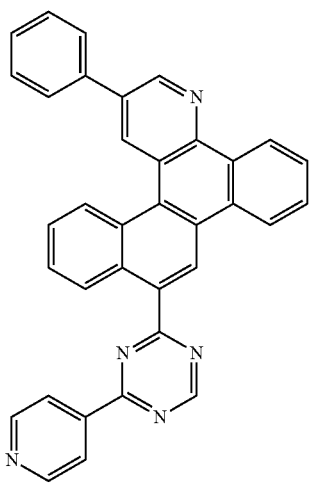
27
30
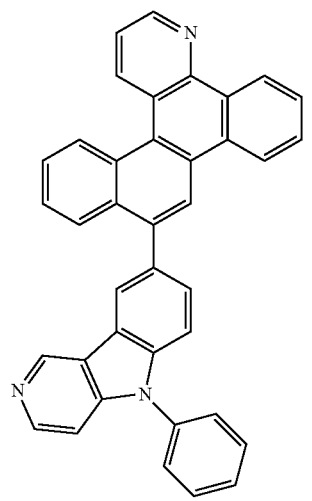

29
-continued
31
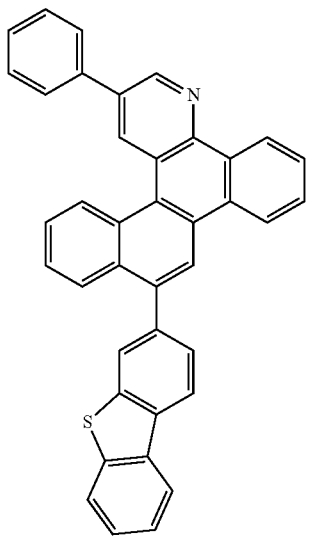
32
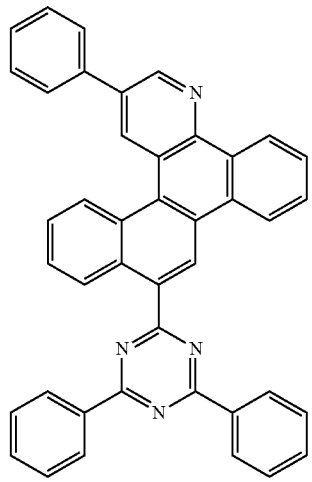
33
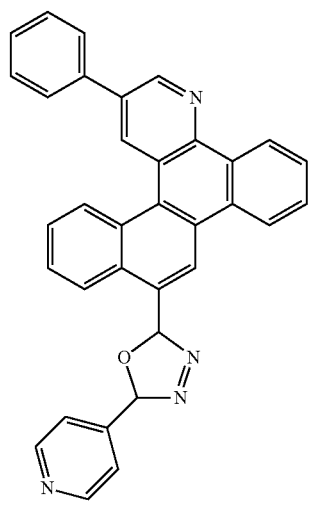
30
-continued
34
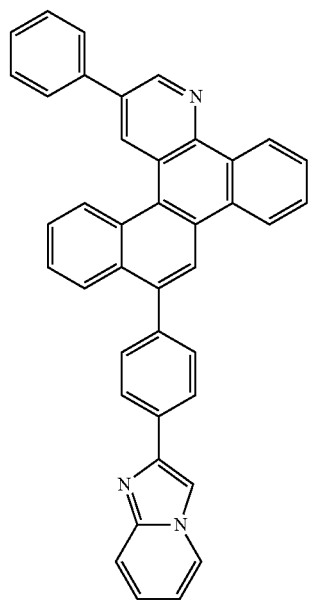
35
36

37
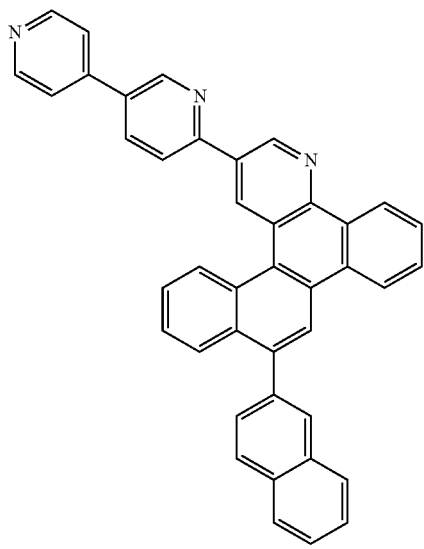
38
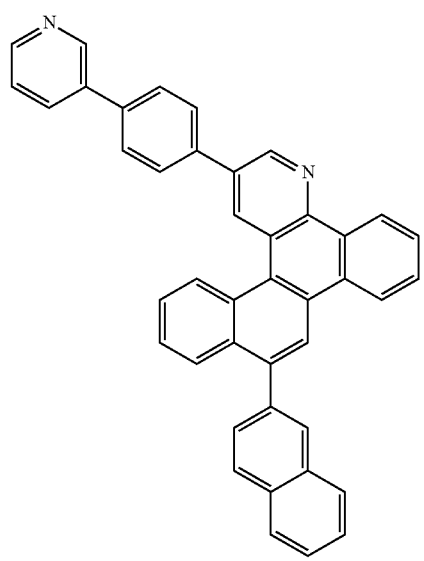
39
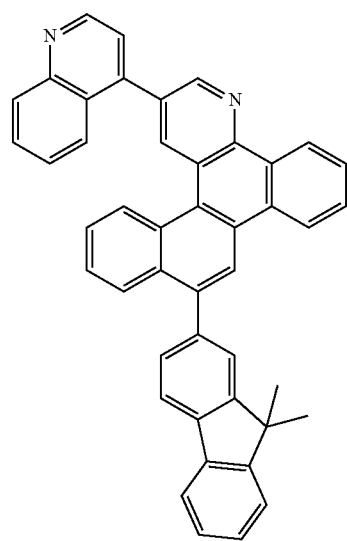
40
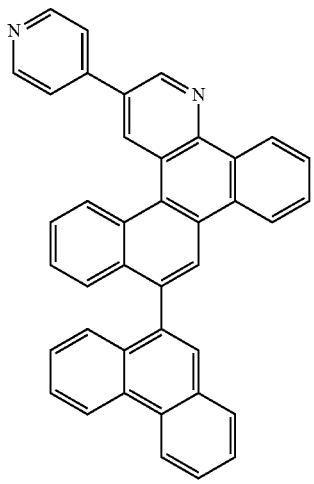
41
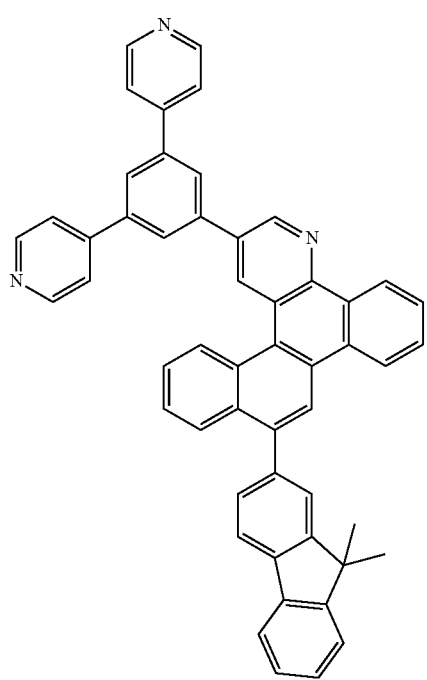

42
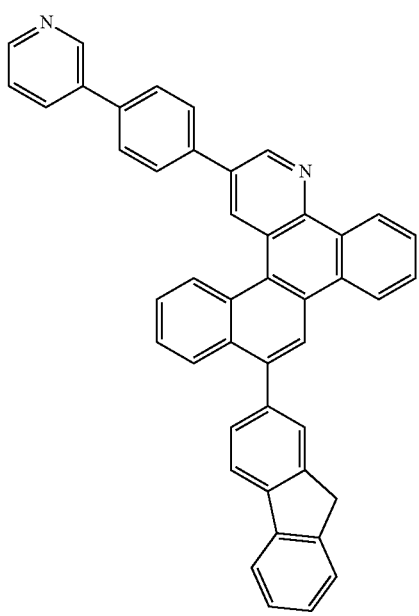
44
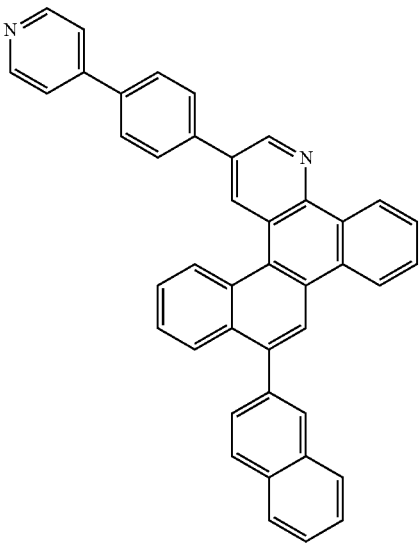
43
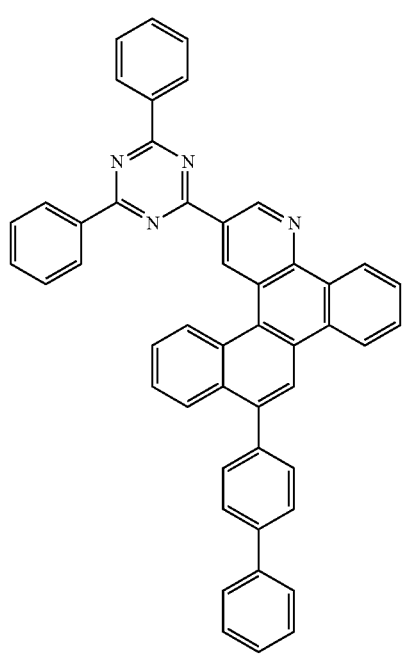
45
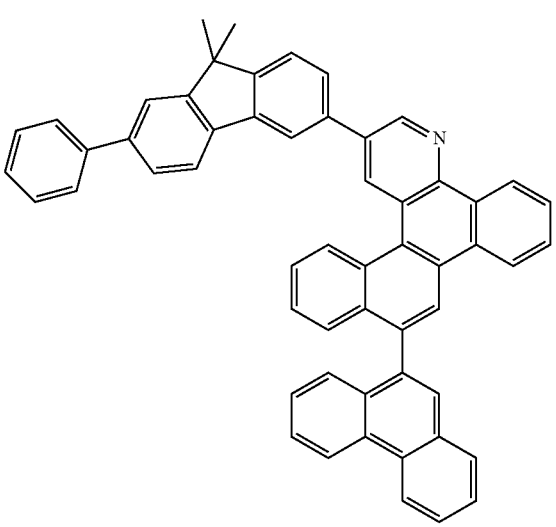

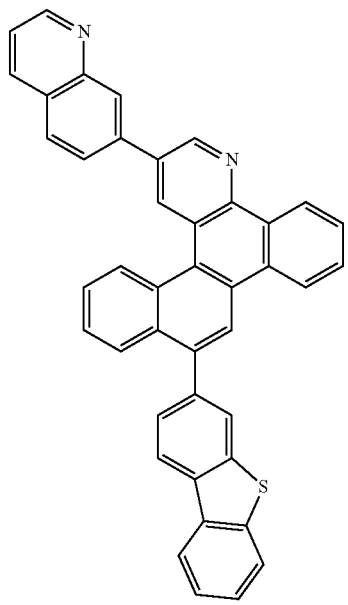
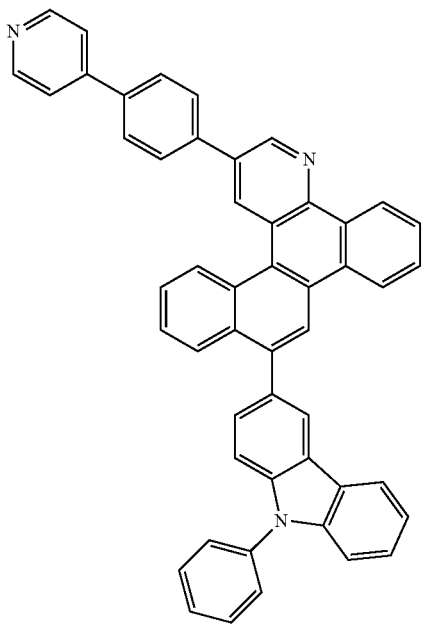

50
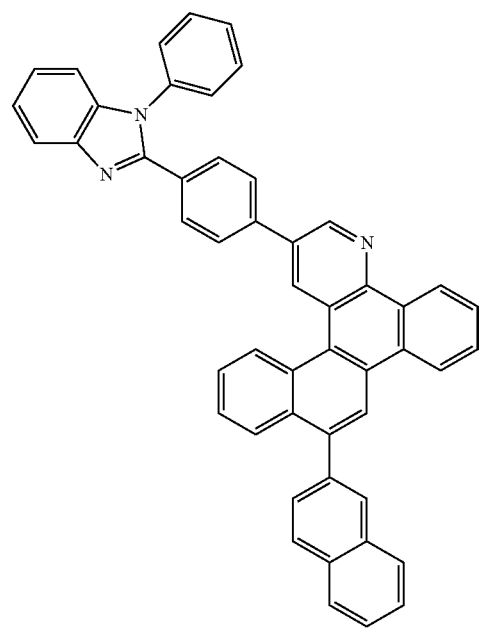
52
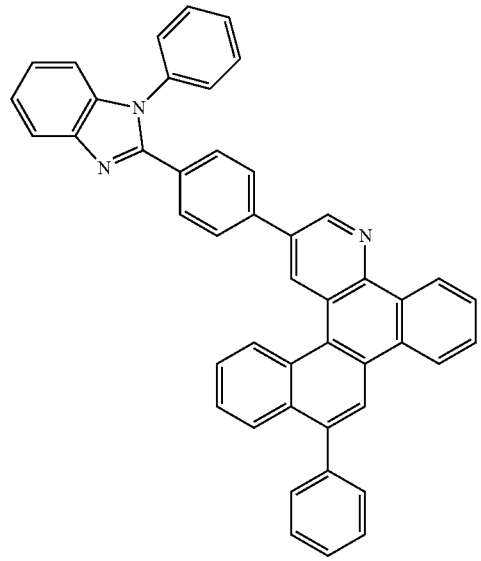
51
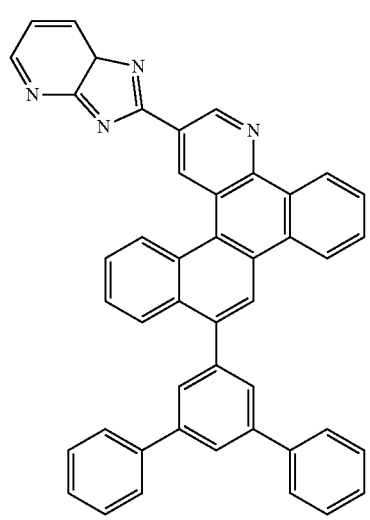
53
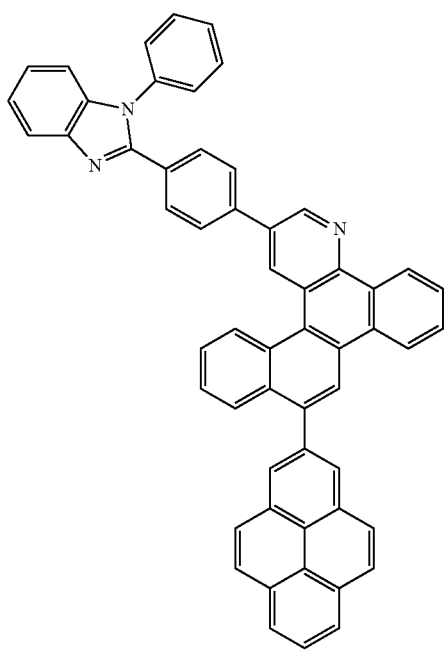

54
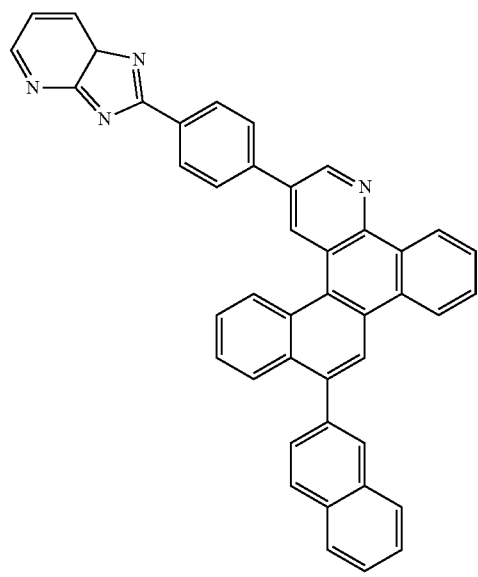
56
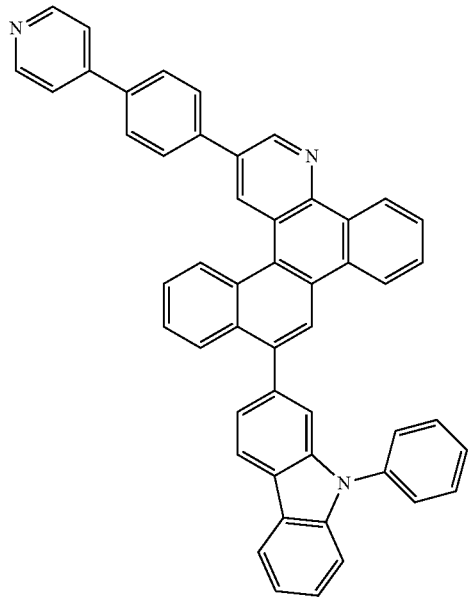
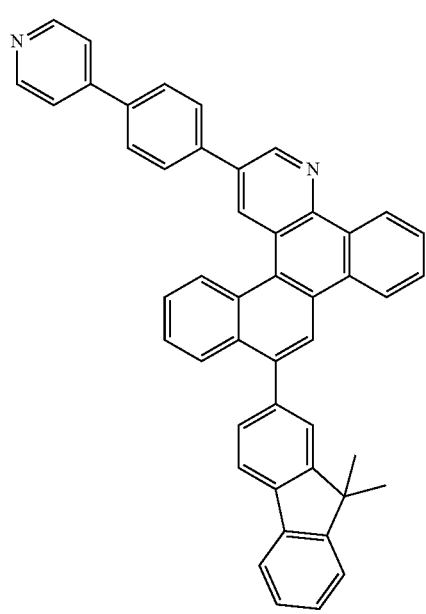
57
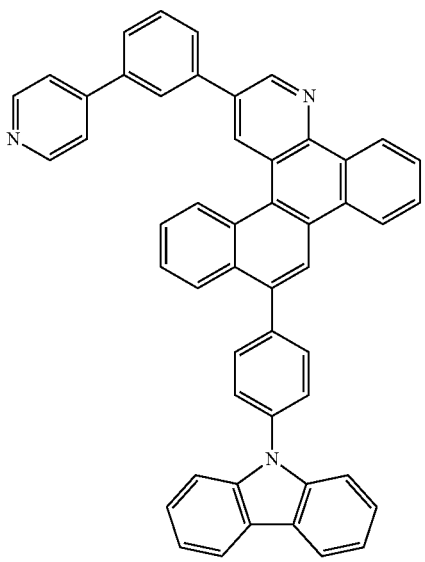

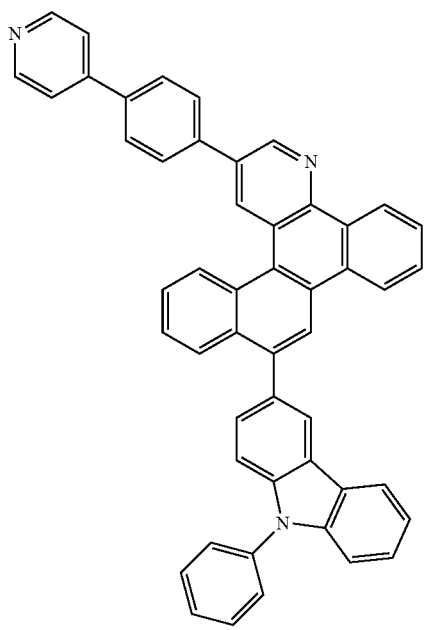
58
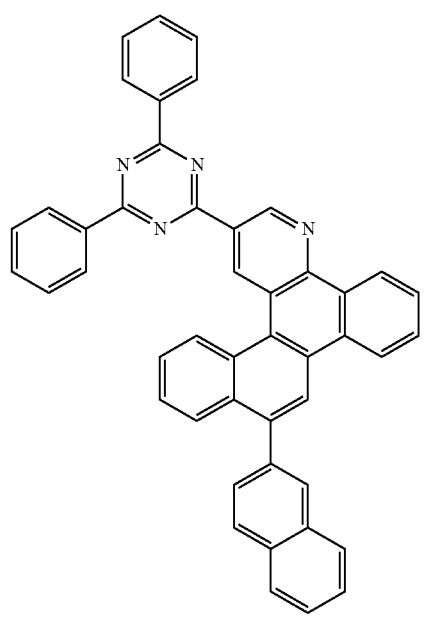
59
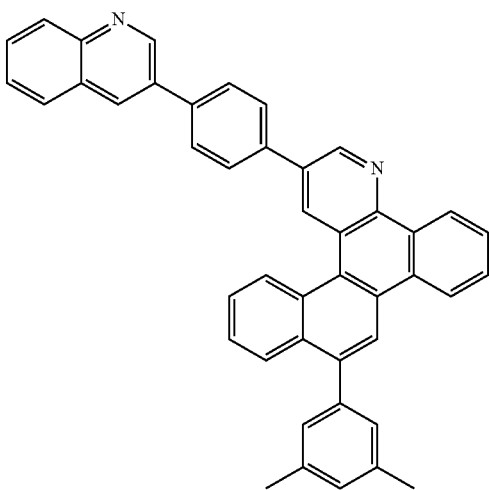
60
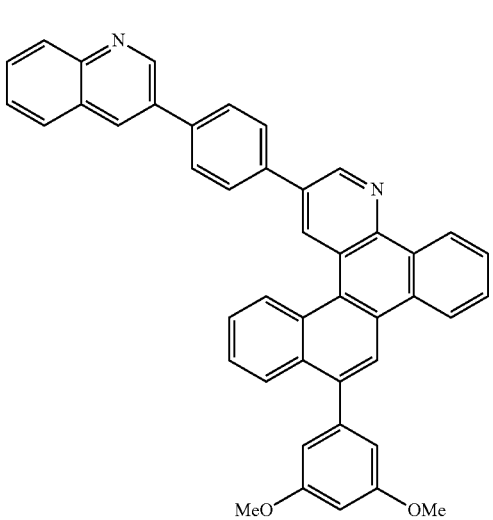
61
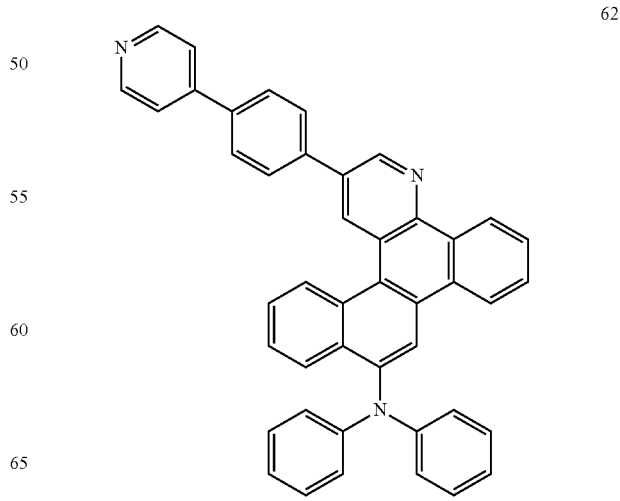
62

63

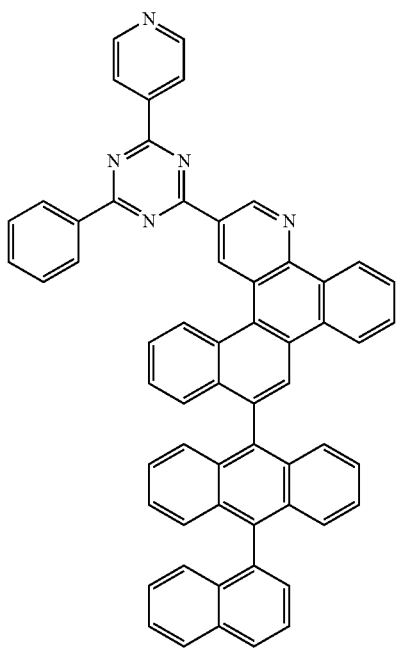

64

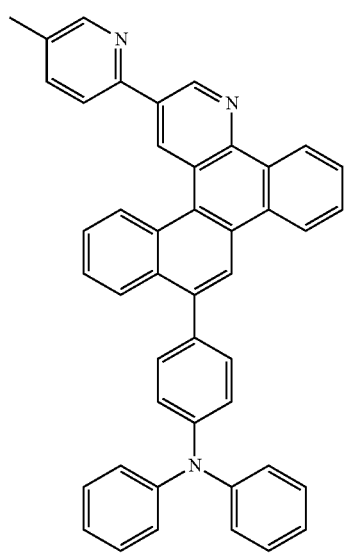

65

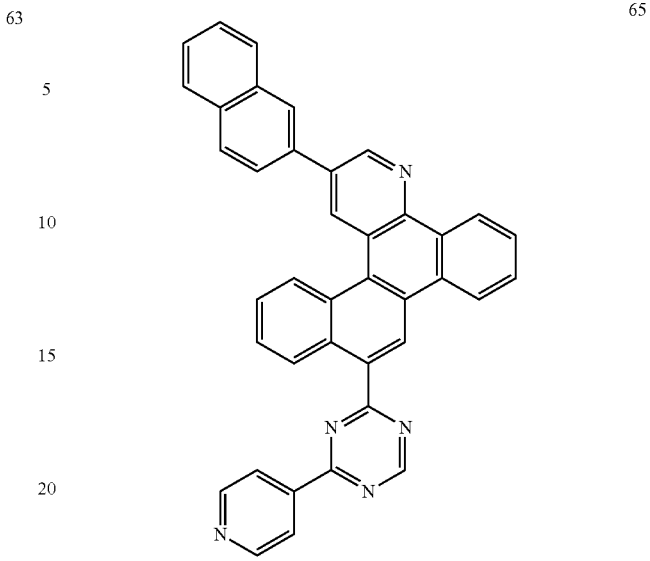

Another aspect of the present invention provides an organic light-emitting device including a first electrode, a second electrode, and an organic layer disposed between the first electrode and the second electrode, wherein the organic layer may include a first layer containing the heterocyclic compound of Formula 1 described above.

The first layer including the heterocyclic compound may include a hole injection layer, a hole transport layer, a functional layer having both hole injection and hole transport capabilities, an electron injection layer, an electron transport layer, or a functional layer having both electron injection and electron transport capabilities.

In some embodiments, the first layer may include at least one layer selected from the group consisting of a hole injection layer, a hole transport layer, a functional layer having both hole injection and hole transport capabilities, an emission layer, an electron injection layer, an electron transport layer, and a functional layer having both electron injection and electron transport capabilities, wherein the first layer may further include a charge generating material.

The charge generating material will be described later.

In some embodiments, the organic layer of the organic light-emitting device may further include, but are not limited to, a hole injection layer, a hole transport layer, a functional layer having both hole injection and hole transport capabilities, an emission layer, a hole blocking layer, an electron transport layer, an electron injection layer, or a combination of at least two thereof. At least one of the hole injection layer, the hole transport layer, and the functional layer having both hole injection and hole transport capabilities may further include a charge generating material for improved layer conductivity, in addition to the heterocyclic compound of Formula 1 described above, a hole injection material and a hole transport material. The emission layer may include a host, and a dopant, for example, a fluorescent dopant or a phosphorescent dopant. The phosphorescent dopant may include iridium (Ir), platinum (Pt), osmium (Os), rhenium (Re), titanium (Ti), zirconium (Zr), hafnium (Hf), or a combination of at least two thereof.

The charge generating material may include, for example, a p-dopant. Non-limiting examples of the p-dopant include quinone derivatives such as tetracyanoquinonedimethane (TCNQ), 2,3,5,6-tetrafluoro-tetracyano-1,4-benzoquinonedimethane (F4TCNQ), and the like; metal oxides such as tungsten oxide, molybdenum oxide, and the like; and cyano-containing compounds such as Compound 100 below.

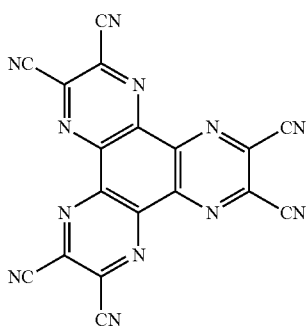

Compound 100

When the hole injection layer, the hole transport layer, or the functional layer having both hole injection and hole transport capabilities further includes a charge generating material, the charge generating material may be, but not limited to, uniformly dispersed or nonuniformly distributed in the layer.

In some embodiments the electron transport layer of the organic light-emitting device may further include an electron-transporting organic compound and a metal-containing material. Non-limiting examples of the electron-transporting organic compound include 9,10-di(naphthalen-2-yl)anthracene (ADN), and anthracene-based compounds, such as Compounds 101 and 102 below.

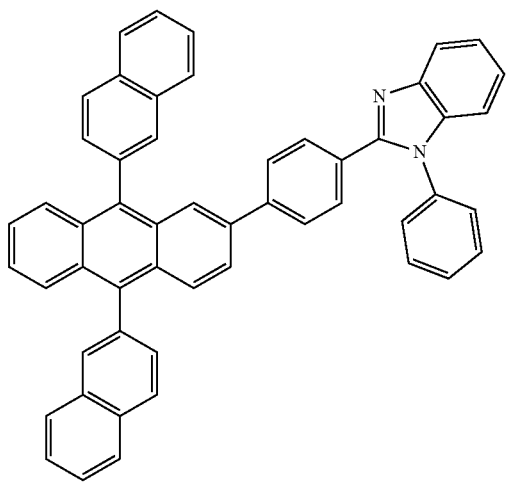

101

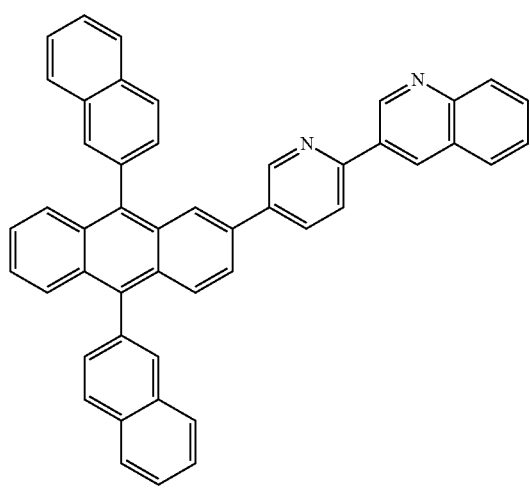

102

The metal-containing material may include a lithium (Li) complex. Non-limiting examples of the Li complex include lithium quinolate (LiQ), Compound 103 below, and the like:

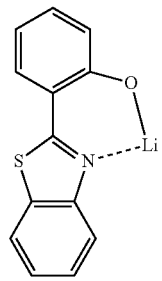

103

The first electrode may be an anode, and the second electrode may be a cathode, but the reverse is also possible.

In some embodiments, the organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. In some other embodiments, the organic light-emitting device may have a first electrode/functional layer having both hole injection and hole transport capabilities/emission layer/electron transport layer/second electrode structure, or a first electrode/functional layer having both hole injection and hole transport capabilities/emission layer/electron transport layer/electron injection layer/second electrode structure. Alternatively, the organic light-emitting device may have a first electrode/hole transport layer/emission layer/functional layer having both electron injection and electron transport capabilities/second electrode structure, a first electrode/hole injection layer/emission layer/functional layer having both electron injection and electron transport capabilities/second electrode structure, or a first electrode/hole injection layer/hole transport layer/emission layer/functional layer having both electron injection and electron transport capabilities/second electrode structure.

According to some embodiments of the present invention, the organic light-emitting device may be either a top-emission organic light-emitting device or a bottom-emission organic light-emitting device.

Hereinafter, a method of manufacturing an organic light-emitting device according to an embodiment of the present invention will be described with reference to FIG. 1. FIG. 1 illustrates the structure of an organic light-emitting device according to an embodiment of the present invention. Referring to FIG. 1, the organic light-emitting device according to the present embodiment includes a substrate (not shown), a first electrode (anode), a hole injection layer (HIL), a hole transport layer (HTL), an emission layer (EML), an electron transport layer (ETL), an electron injection layer (EIL), and a second electrode (cathode).

First, a first electrode is formed on a substrate by using a deposition or sputtering method. The first electrode may be formed of a first electrode material having a high work function. The first electrode may constitute an anode or a cathode. The substrate may be a substrate conventionally used in organic light-emitting devices, and may include, for example, a glass substrate or a transparent plastic substrate with excellent mechanical strength, thermal stability, transparency, surface smoothness, ease of handling, and water resistance. Examples of the first electrode material include materials, such as indium tin oxide (ITO), indium zinc oxide (IZO), tin oxide ($SnO_2$), zinc oxide (ZnO), aluminum (Al), silver (Ag), and magnesium (Mg), which have excellent conductivity. The first electrode may be formed as a transparent or reflective electrode.

Next, the HIL may be formed on the first electrode using various methods, for example, by vacuum deposition, spin coating, casting, Langmuir-Blodgett (LB) deposition, or the like.

When the HIL is formed using vacuum deposition, the deposition conditions may vary according to a material that is used to form the HIL, and the structure and thermal characteristics of the HIL. For example, the deposition conditions may include a deposition temperature of about 100 to about 500° Q a vacuum pressure of about $10^{-8}$ to about $10^{-3}$ torr, and a deposition rate of about 0.01 to about 100 Å/sec.

When the HIL is formed using spin coating, coating conditions may vary according to the material used to form the HIL, and the structure and thermal properties of the HIL. For example, the coating conditions may include a coating speed of about 2,000 rpm to about 5,000 rpm, and a thermal treatment temperature of about 80° C. to about 200° C. at which the solvent remaining after coating may be removed.

The HIL may be formed of the heterocyclic compound of Formula 1 or any material that is commonly used to form a HIL. Non-limiting examples of the material that can be used to form the HIL include a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

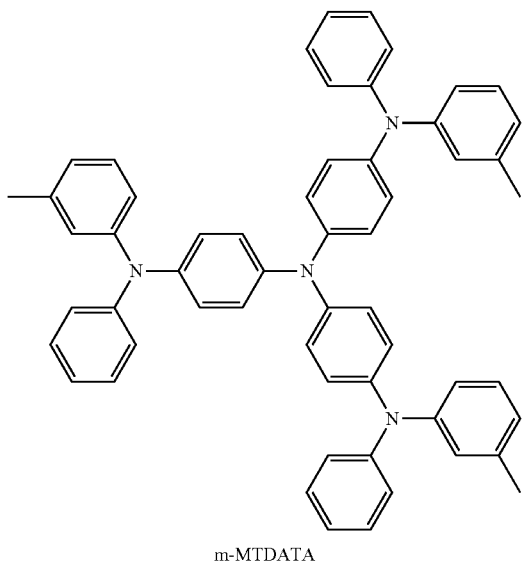

m-MTDATA

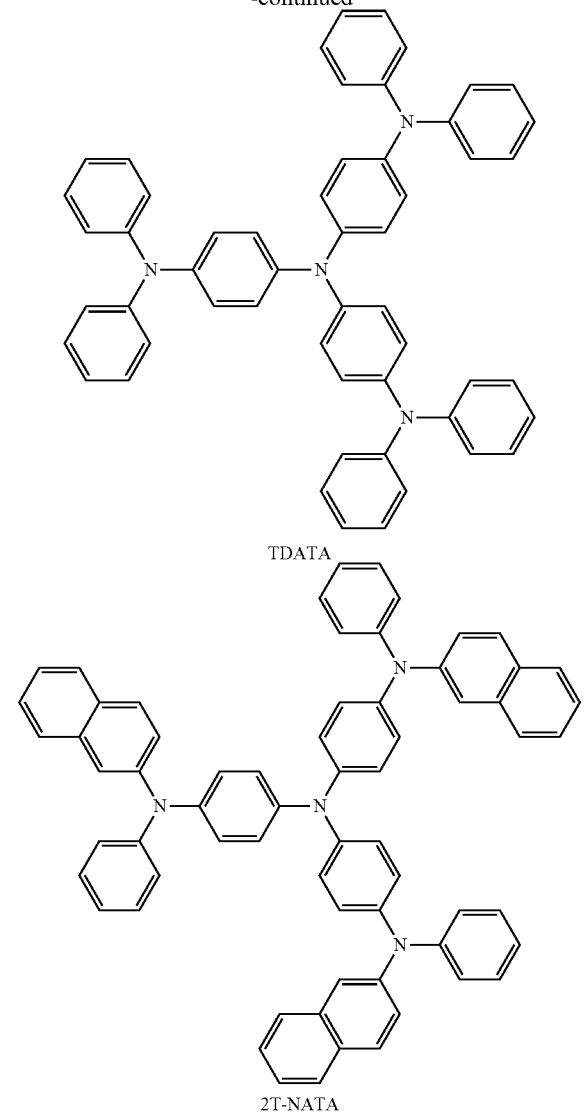

TDATA

2T-NATA

The HIL may have a thickness of about 100 Å to about 10,000 Å, and in some other embodiments, may have a thickness of about 100 Å to about 1,000 Å. When the thickness of the HIL is within these ranges, the HIL may have good hole injection characteristics without an increase in driving voltage.

Next, the HTL may be formed on the HIL using any of a variety of methods, for example, vacuum deposition, spin coating, casting, LB deposition, or the like. When the HTL is formed using vacuum deposition or spin coating, the deposition or coating conditions may be similar to those applied to form the HIL, though the deposition or coating conditions may vary according to the material that is used to form the HTL.

The HTL may be formed of the heterocyclic compound of Formula 1 or any known HTL material. Non-limiting examples of such HTL materials include carbazole derivatives such as N-phenylcarbazole or polyvinylcarbazole, and amine derivatives having an aromatic condensed ring, such as NPB, N,N'-bis(3-methylphenyl)-N,N'-diphenyl-[1,1-biphenyl]-4,4'-diamine (TPD).

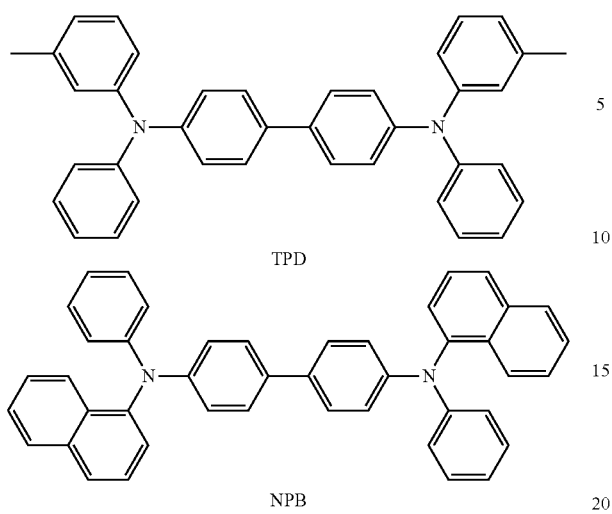

TPD

NPB

The HTL may have a thickness of about 50 Å to about 1,000 Å, and in some embodiments, may have a thickness of about 100 Å to about 600 Å. When the thickness of the HTL is within these ranges, the HTL may have good hole transport characteristics without a substantial increase in driving voltage.

Next, the EML may be formed on the HTL using any of a variety of methods, for example, by vacuum deposition, spin coating, casting, LB deposition, or the like. When the EML is formed using vacuum deposition or spin coating, the deposition or coating conditions may be similar to those applied to form the HIL, though the deposition or coating conditions may vary according to the material that is used to form the EML.

The EML may include the heterocyclic compound of Formula 1 described above. The EML may be formed using any known light-emitting material, such as known hosts and dopants. Dopants that may be used to form the EML may include either a fluorescent dopant or a phosphorescent dopant which are widely known in the art.

Non-limiting examples of the host include Alq3, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, and distyrylarylene (DSA).

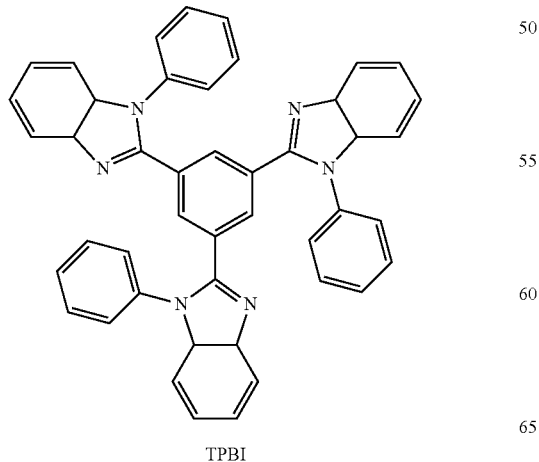

TPBI

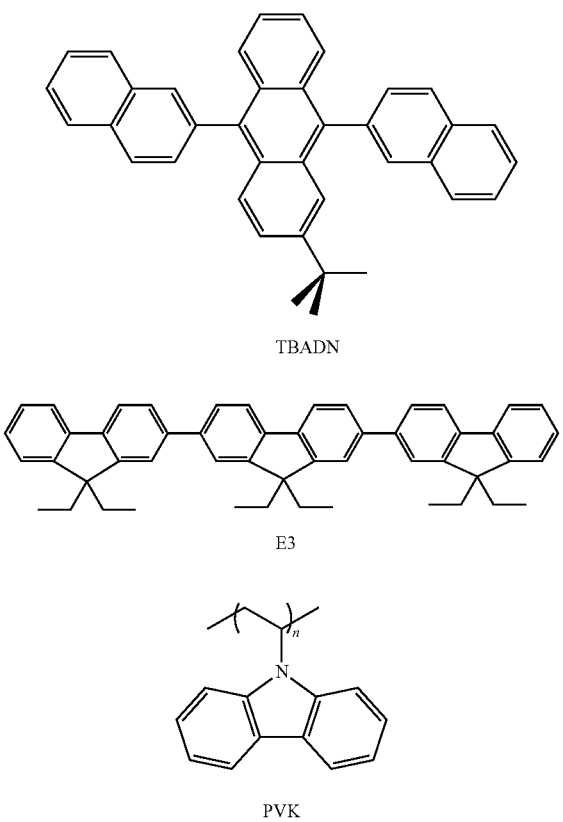

TBADN

E3

PVK

Examples of red dopants include, but are not limited to, platinum(H) octaethylporphyrin (PtOEP), Ir(piq)$_3$, Btp$_2$Ir(acac), and DCJTB.

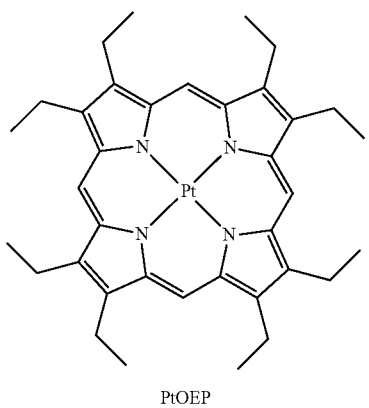

PtOEP

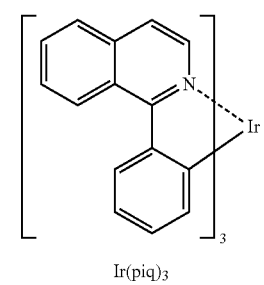

Ir(piq)$_3$

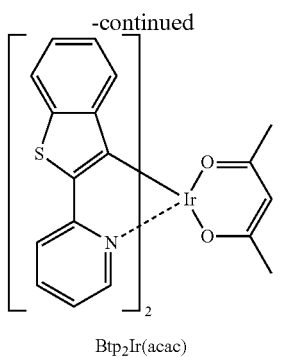

Btp₂Ir(acac)

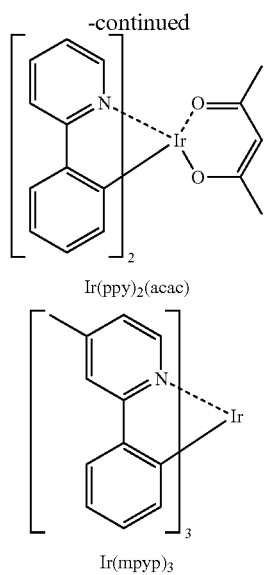

Ir(ppy)₂(acac)

Ir(mpyp)₃

Examples of green dopants may include, but are not limited to, Ir(ppy)₃ (where "ppy" denotes phenylpyridine), Ir(ppy)₂(acac), Ir(mpyp)₃, and C545T.

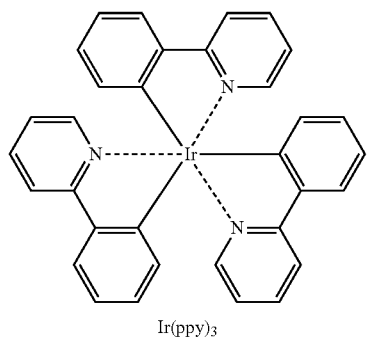

Ir(ppy)₃

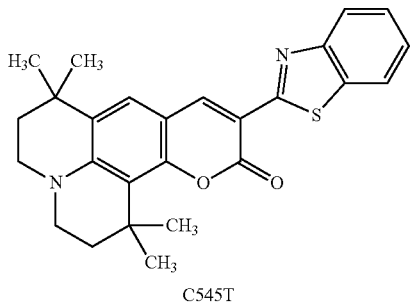

C545T

Examples of blue dopants include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl phenylene (TBP), but are not limited thereto.

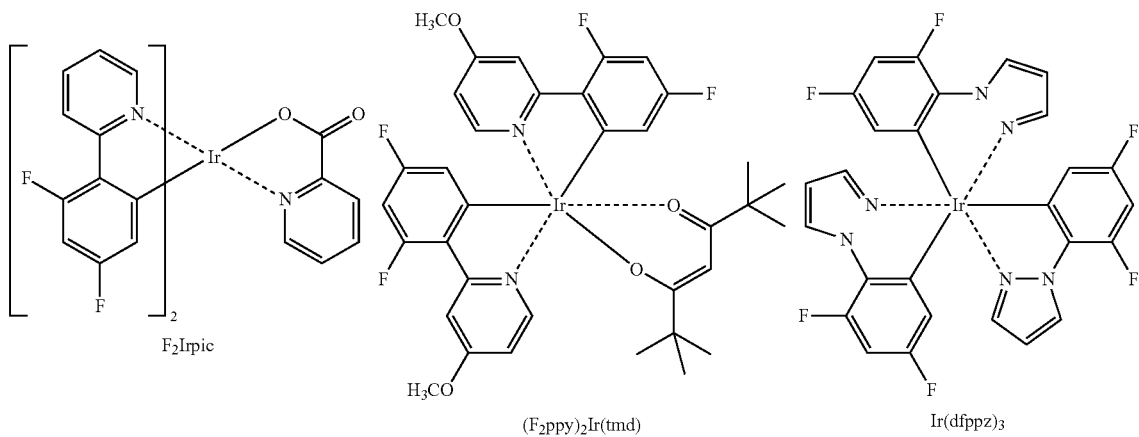

F₂Irpic     (F₂ppy)₂Ir(tmd)     Ir(dfppz)₃

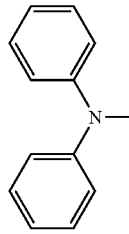

DPAVBi

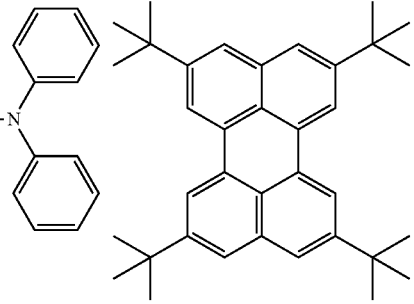

TBP

The amount of the dopant may be from about 0.1 to about 20 parts by weight, and in some other embodiments, may be from about 0.5 to about 12 parts by weight, based on 100 parts by weight of the EML material, which is equivalent to the total weight of the host and the dopant. When the amount of the dopant is within these ranges, concentration quenching may be substantially prevented.

The EML may have a thickness of about 100 Å to about 1,000 Å, and in some embodiments, may have a thickness of about 200 Å to about 600 Å When the thickness of the EML is within these ranges, the EML may have good light-emitting characteristics without a substantial increase in driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may be formed of any material commonly used to form a HBL. Examples of such HBL materials include, but are not limited to, oxadiazole derivatives, triazole derivatives, phenathroline derivatives, Balq, and BCP.

The HBL may have a thickness of about 50 Å to about 1,000 Å, and in some embodiment, may have a thickness of about 100 Å to about 300 Å. When the thickness of the HBL is within these ranges, the HBL may have good hole blocking characteristics without a substantial increase in driving voltage.

Next, the ETL is formed on the EML (or HBL) using various methods, for example, by vacuum deposition, spin coating, casting, or the like. When the ETL is formed using vacuum deposition or spin coating, the deposition or coating conditions may be similar to those applied to form the HIL, though the deposition or coating conditions may vary according to the material that is used to form the ETL.

The ETL material may include the heterocyclic compound of Formula 1 described above. Alternatively, the ETL may be formed of any material that is widely known in the art. Examples of the ETL material include, but are not limited to, quinoline derivatives, such as tris(8-quinolinolate)aluminum (Alq3), TAZ, and BAlq.

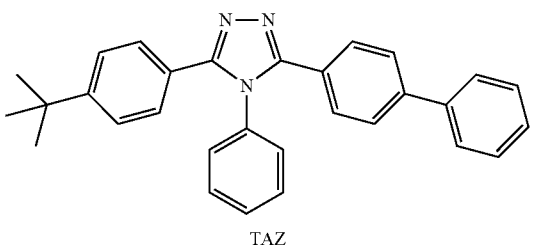

TAZ

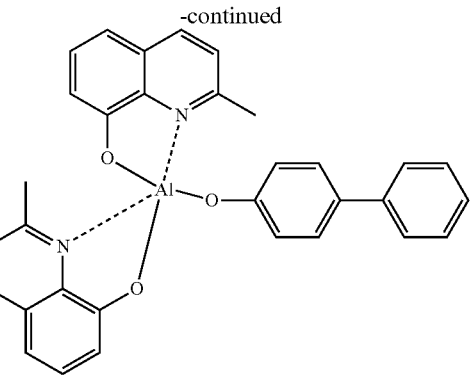

BAlq

The ETL may have a thickness of about 100 Å to about 1,000 Å, and in some other embodiments, may have a thickness of about 100 Å to about 500 Å. When the thickness of the ETL is within these ranges, the ETL may have good electron transport characteristics without a substantial increase in driving voltage.

In addition, the EIL, which facilitates injection of electrons from the cathode, may be formed on the ETL.

The EIL may be formed of the heterocyclic compound of Formula 1 described above, or any known materials used to form an EIL layer, for example, LiF, NaCl, CsF, $Li_2O$, BaO, or the like. The deposition or coating conditions may be similar to those applied to form the HIL, although the deposition and coating conditions may vary according to the material that is used to form the EIL.

The EIL may have a thickness of about 1 Å to 100 Å, and in some embodiments, may have a thickness of about 5 Å to about 90 Å. When the thickness of the EIL is within these ranges, the EIL may have good electron injection characteristics without a substantial increase in driving voltage.

Finally, the second electrode may be formed on the EIL by using, for example, vacuum deposition, sputtering, or the like. The second electrode may constitute a cathode or an anode. The material for forming the second electrode may include a metal, an alloy, or an electrically conductive compound, which are materials having a low work function, or a mixture thereof. Examples of such materials include, but are not limited to, lithium (Li); magnesium (Mg), aluminum (Al), aluminum-lithium (Al—Li), calcium (Ca), magnesium-indium (Mg—In), and magnesium-silver (Mg—Ag). In addition, in order to manufacture a top-emission organic light-emitting device, a transparent cathode formed of a transparent material such as ITO or IZO may be used as the second electrode.

According to embodiments of the present invention, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some embodiments the first layer of the organic light-emitting device may be formed of the heterocyclic compound of Formula 1 by using a deposition method or may be formed using a wet method of coating a solution of the heterocyclic compound of Formula 1.

Hereinafter, the present invention will be described in detail with reference to synthesis examples of Compounds 3, 8, 18, 37, 53 and 65 and other examples. However, these examples are for illustrative purposes only and are not intended to limit the scope of the present invention.

EXAMPLES

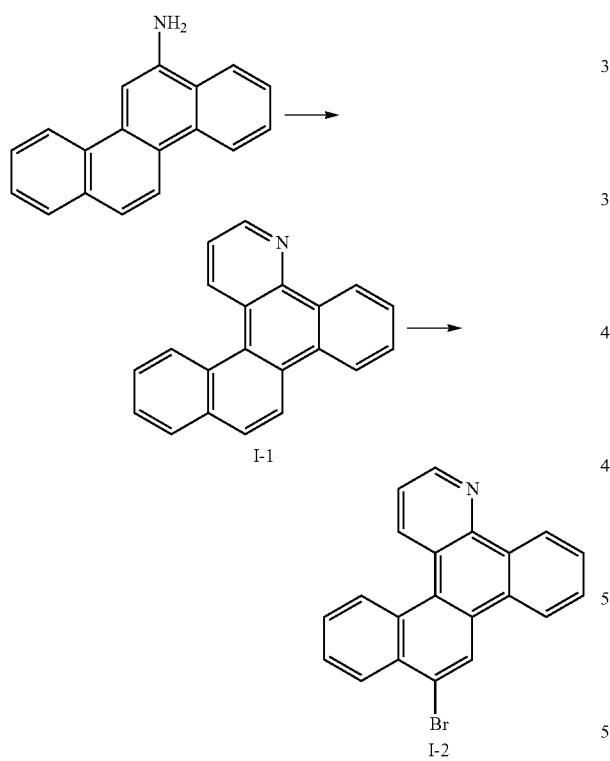

Synthesis Example 1

Synthesis of Compound 3

Synthesis of Intermediate I-1

2.43 g (10 mmol) of 6-aminochrysene and 760 mg (10 mmol) of 1,3-protane diol were dissolved in 10 ml of mesitylene. 0.240 g (0.4 mmol) of $IrCl_3 \cdot H_2O$, 36 mg (0.6 mmol) of 2,2'-bis-diphenylphosphino-1,1'-binaphtyl (BINAP), and 0.064 g (0.6 mmol) of $Na_2CO_3$ were added to the solution, and then stirred at about 170° C. for about 15 hours. The mixture was concentrated, and the residue was separated and purified using silica gel column chromatography to obtain 2.56 g of Intermediate I-1 (Yield: 92%) This compound was identified using liquid chromatography-mass spectroscopy (LC-MS).

$C_{21}H_{13}N$ calc.: 279.1. found [M+1] 280.1

Synthesis of Intermediate I-2

4.19 g (15.0 mmol) of Intermediate I-1 was dissolved in 100 mL of dichloromethane to obtain a solution, and 1.75 mL (15.0 mmol) of bromine ($Br_2$) was slowly dropwise added to the solution at about 0° C. to obtain a reaction solution. The reaction solution was stirred at room temperature for about 12 hours. 60 mL of water and 30 mL of a 20% aqueous thiosodium sulfate solution were added to the reaction solution, followed by three times of extraction with 80 mL of dichloromethane. The organic phase was collected, and was dried using magnesium sulfate to evaporate the solvent. The residue was separated and purified by silica gel column chromatography, followed by recrystallization with a dichloromethane/hexane solution to obtain 3 g of Intermediate I-2 (Yield 56%). This compound was identified using LC-MS.

$C_{21}H_{12}BrN$ calc.: 357.0. found [M+1] 358.0

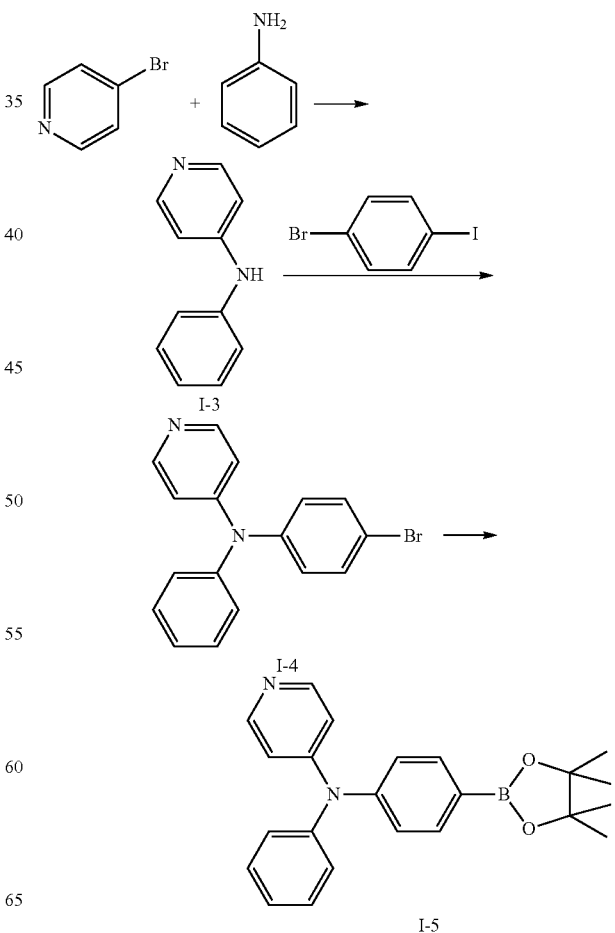

Synthesis of Intermediate I-3

3.16 g (20.0 mmol) of 4-bromopyrine, 2.79 g (30.0 mmol) of aniline, 0.37 g (0.4 mmol) of $Pd_2(dba)_3$, 0.08 g (0.4 mmol) of $PtBu_3$, and 2.88 g (30.0 mmol) of KOtBu were dissolved in 60 mL of toluene to obtain a solution, which was then stirred at about 85° C. for about 4 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 1.49 g of Intermediate I-3 (Yield: 88%) This compound was identified using LC-MS. $C_{11}H_{10}N$ calc.: 170.1. found [M+1] 171.1

Synthesis of Intermediate I-4

2.55 g (15.0 mmol) of Intermediate I-3, 2.83 g (10.0 mmol) of 4-bromoiodobenzene, 0.18 g (0.2 mmol) of $Pd_2(dba)_3$, 0.04 g (0.4 mmol) of $PtBu_3$, and 1.44 g (15.0 mmol) of KOtBu were dissolved in 40 mL of toluene to obtain a solution, which was then stirred at about 85° C. for about 4 hours. The reaction solution was cooled to room temperature, followed by three times of extraction with 30 mL of water and 30 mL of diethylether. The organic phase was collected, and was dried using magnesium sulfate to evaporate the solvent. The residue was separated and purified using silica gel column chromatography to obtain 2.04 g of Intermediate I-4 (Yield: 63%) This compound was identified using LC-MS. $C_{17}H_{13}BrN_2$ calc.: 324.0. found [M+1] 325.0

Synthesis of Intermediate I-5

3.25 g (10.0 mmol) of Intermediate I-4, 2.54 g (10.0 mmol) of bis(pinacolato)diborone, 0.36 g (0.5 mmol) of $PdCl_2(dppf)_2$, and 2.94 g (30.0 mmol) of KOAc were dissolved in 40 mL of DMSO to obtain a solution, which was then stirred at about 80° C. for about 6 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 2.97 g of Intermediate I-5 (Yield: 80%) This compound was identified using LC-MS. $C_{23}H_{25}BN_2O_2$ calc.: 372.2. found [M+1] 373.2

Synthesis of Compound 3

1.79 g (5.0 mmol) of Intermediate I-2, 1.86 g (5.0 mmol) of Intermediate I-5, 0.29 g (0.25 mmol) of $Pd(PPh_3)_4$, and 2.07 g (15.0 mmol) of $K_2CO_3$ were dissolved in 30 mL of a mixed solution $THF/H_2O$ (2:1), which was then stirred at about 70° C. for about 5 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 1.49 g of Compound 3 (Yield: 69%) This compound was identified using high-resolution mass spectrometry (HR-MS). $C_{32}H_{20}N_2$ calc.: 432.1626. found [M+1] 437.1626

$^1$H NMR ($CDCl_3$, 400 MHz) δ (ppm) 9.59-9.54 (m, 1H), 9.02 (s, 1H), 8.90-8.89 (d, 1H), 8.83 (d, 1H), 8.75-8.74 (d, 2H), 8.69-8.67 (m, 1H), 8.25-8.23 (d, 1H), 8.10 (d, 1H), 7.88-7.86 (d, 1H), 7.84-7.81 (m, 2H), 7.71-7.67 (m, 2H), 7.60-7.58 (m, 1H), 7.55-7.53 (d, 2H), 7.42-7.40 (dd, 1H), 7.36-7.32 (t, 1H), 7.19-7.15 (t, 1H)

Synthesis Example 2

Synthesis of Compound 8

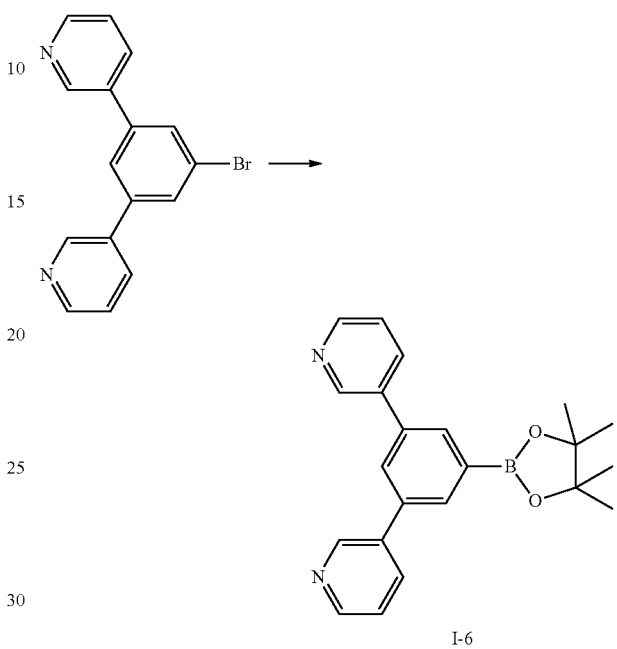

I-6

Synthesis of Intermediate I-6

2.86 g of Intermediate I-6 was synthesized using 3,3'-(5-bromo-1,3-phenylene)dipyridine in the same manner as in the synthesis of Intermediate I-5 (Yield: 80%). This compound was identified using LC-MS. $C_{22}H_{23}BN_2O_2$ calc.: 358.2. found [M+1] 359.2

Synthesis of Compound 8

3.26 g of Compound 8 was synthesized using Intermediate I-2 and Intermediate I-6 in the same manner as in the synthesis of Compound 3. This compound was identified using HR-MS. $C_{37}H_{23}N_3$ calc.: 509.1892. found [M+1] 510.1892

$^1$H NMR ($CDCl_3$, 400 MHz) δ (ppm) 9.59-9.54 (m, 1H), 8.95 (m, 3H), 8.90-8.89 (d, 1H), 8.83-8.80 (d, 1H), 8.72-8.66 (m, 3H), 8.40-8.38 (d, 1H), 8.10-8.08 (m, 3H), 8.04 (s, 2H), 7.90-7.89 (d, 1H), 7.84-7.80 (m, 2H), 7.71-7.67 (t, 1H), 7.50-7.46 (dd, 2H), 7.42-7.39 (dd, 1H), 7.25-7.21 (t, 1H))

Synthesis Example 3

Synthesis of Compound 18

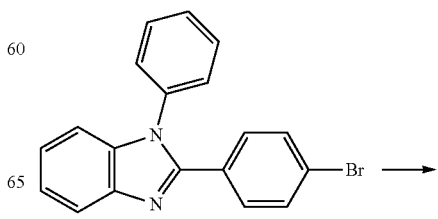

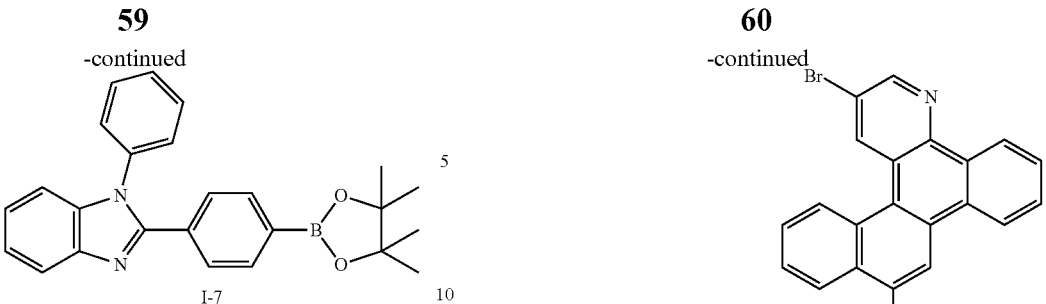

I-7

Synthesis of Intermediate I-7

3.09 g of Intermediate I-7 was synthesized using 2-(4-bromophenyl)-1-phenyl-benzoimidazole in the same manner as in the synthesis of Intermediate I-5 (Yield: 78%). This compound was identified using LC-MS. $C_{25}H_{25}BN_2O_2$ calc.: 396.3. found [M+1.] 397.3

Synthesis of Compound 18

1.93 g of Compound 18 was synthesized using Intermediate I-2 and Intermediate I-7 in the same manner as in the synthesis of Compound 3 (Yield: 71%). This compound was identified using HR-MS. $C_{40}H_{25}N_3$ calc.: 547.6466. found [M+1] 548.6466

$^1$H NMR (CDCl$_3$, 400 MHz) δ (ppm) 9.59-9.54 (m, 1H), 9.09 (s, 1H), 8.90-8.89 (d, 1H), 8.83-8.82 (m, 2H), 8.71-8.67 (m, 1H), 8.20-8.17 (d, 2H), 7.85-7.82 (m, 5H), 7.80-7.78 (d, 1H), 7.71-7.66 (dd, 2H), 7.57-7.52 (m, 2H), 7.44-7.37 (m, 4H), 7.30 (t, 1H), 7.24-7.21 (t, 1H), 7.16-7.13 (t, 1H))

Synthesis Example 4

Synthesis of Compound 37

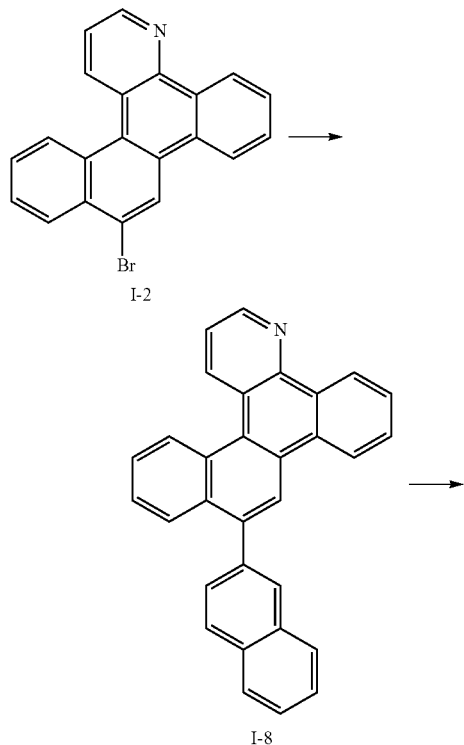

Synthesis of Intermediate I-8

1.79 g (5.0 mmol) of Intermediate I-2, 0.85 g (5.0 mmol) of 2-naphtalene boronic acid, 0.29 g (0.25 mmol) of Pd(PPh$_3$)$_4$, and 2.07 g (15.0 mmol) of K$_2$CO$_3$ were dissolved in 30 mL of a mixed solution THF/H$_2$O (2:1), which was then stirred at about 70° C. for about 5 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 1.78 g of Intermediate I-8 (Yield: 88%) This compound was identified using LC-MS. $C_{31}H_{19}N$ calc.: 405.2. found [M+1] 406.2

Synthesis of Intermediate I-9

6.08 g (15.0 mmol) of Intermediate I-8 was dissolved in 100 mL of dichloromethane to obtain a solution, and 1.75 mL (15.0 mmol) of bromine (Br$_2$) was slowly dropwise added to the solution at about 0° C. to obtain a reaction solution. The reaction solution was stirred at room temperature for about 12 hours. 60 mL of water and 30 mL of a 20% aqueous thiosodium sulfate solution were added to the reaction solution, followed by three times of extraction with 80 mL of dichloromethane. The organic phase was collected, and was dried using magnesium sulfate to evaporate the solvent. The residue was separated and purified by silica gel column chromatography, followed by recrystallization with a dichloromethane/hexane solution to obtain 3.77 g of Intermediate I-9 (Yield 52%). This compound was identified using LC-MS. $C_{31}H_{18}BrN$ calc.: 483.1. found [M+1] 484.1

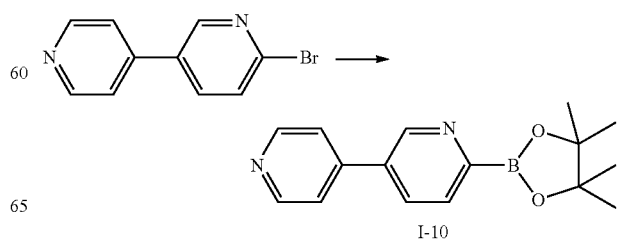

Synthesis of Intermediate I-10

2.28 g of Intermediate I-10 was synthesized using 6-bromo-3,4'-bipyridine in the same manner as in the synthesis of Intermediate I-5 (Yield: 81%). This compound was identified using LC-MS. $C_{16}H_{19}BN_2O_2$ calc: 282.2. found [M+1] 283.2

Synthesis of Compound 37

2.09 g of Compound 37 was synthesized using Intermediate I-9 and Intermediate 1-10 in the same manner as in the synthesis of Compound 3 (Yield: 75%). This compound was identified using HR-MS. $C_{41}H_{25}N_3$ calc. 559.2048. found [M+1] 560.2048

$^1$H NMR (CDCl$_3$, 400 MHz) δ (ppm) 9.78-9.74 (m, 1H), 9.68 (s, 1H), 9.38 (d, 1H), 9.16 (d, 1H), 9.12 (s, 1H), 8.75-8.71 (m, 1H), 8.67-8.65 (m, 2H), 8.32-8.30 (d, 1H), 8.21-8.19 (d, 1H), 8.15 (s, 1H), 8.05-8.03 (d, 1H), 8.00-7.98 (d, 1H), 7.88-7.81 (m, 6H), 7.73-7.69 (t, 1H), 7.60-7.52 (m, 2H), 7.43-7.41 (d, 2H), 7.19-7.15 (t, 1H)

Synthesis Example 5

Synthesis of Compound 53

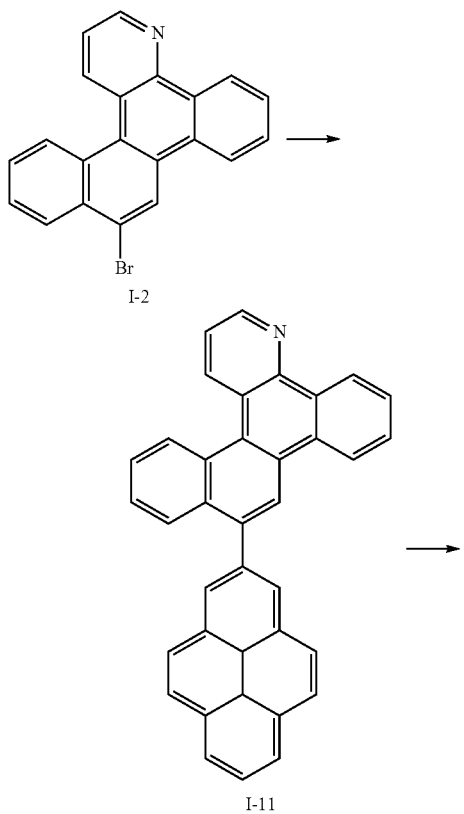

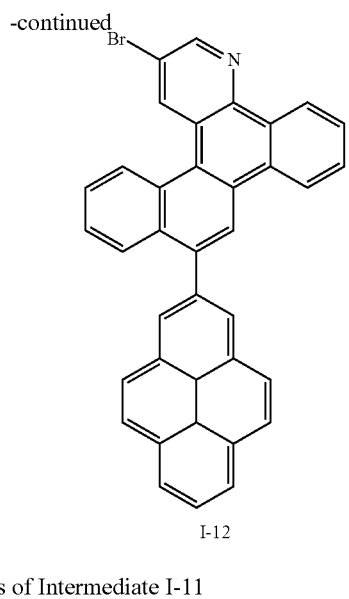

I-12

Synthesis of Intermediate I-11

1.87 g of Intermediate I-11 was synthesized using 2-pyrene boronic acid, instead of 2-naphtalene boronic acid, in the same manner as in the synthesis of Intermediate I-8 (Yield: 78%). This compound was identified using LC-MS. $C_{37}H_{23}N$ calc.: 481.2. found [M+1] 482.2

Synthesis of Intermediate I-12

4.62 g of Intermediate I-12 was synthesized using Intermediate 1-11 in the same manner as in the synthesis of Intermediate I-9 (Yield: 55%). This compound was identified using liquid chromatography-mass spectroscopy (LC-MS). $C_{37}H_{22}BrN$ calc.: 559.1. found [M+1] 560.1

Synthesis of Compound 53

2.61 g of Compound 53 was synthesized using Intermediate I-7 and Intermediate 1-12 in the same manner as in the synthesis of Compound 3 (Yield: 70%). This compound was identified using HR-MS. $C_{56}H_{33}N_3$ calc.: 747.2674. found [M+1] 748.2674

$^1$H NMR (CDCl$_3$, 400 MHz) δ (ppm) 9.78-9.73 (m, 1H), 9.14 (s, 1H), 9.09 (s, 1H), 9.04 (s, 1H), 8.75-8.70 (m, 1H), 8.49-8.47 (d, 1H), 8.41 (s, 2H), 8.23-8.21 (d, 2H), 8.16-8.14 (m, 2H), 8.10-8.02 (m, 4H), 7.96-7.94 (d, 2H), 7.85-7.78 (m, 4H), 7.73-7.69 (t, 1H), 7.66-7.64 (d, 1H), 7.57-7.52 (m, 2H), 7.44-7.35 (m, 4H), 7.32-7.28 (t, 1H), 7.25-7.21 (t, 2H)

Synthesis Example 6

Synthesis of Compound 65

-continued

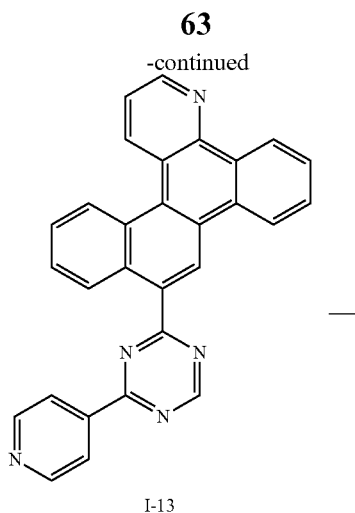

I-13

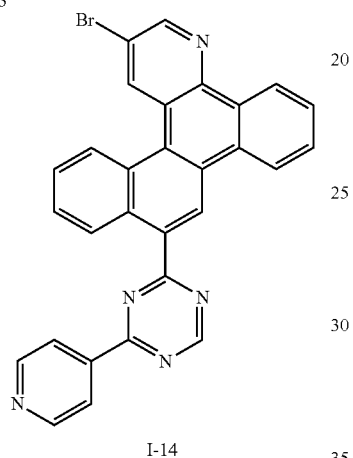

I-14

Synthesis of Intermediate I-13

1.54 g of Intermediate I-13 was synthesized using 2-(pyridine-4-yl)-4-(4,4,5,5-tetramethyl-1,3,2-dioxaborolan-2-yl)-1,3,5-tetrazine, instead of 2-naphtalene boronic acid, in the same manner as in the synthesis of Intermediate I-8 (Yield: 71%). This compound was identified using LC-MS. $C_{29}H_{17}N_5$ calc.: 435.1. found [M+1] 436.1

Synthesis of Intermediate I-14

4.78 g of Intermediate I-14 was synthesized using Intermediate I-13 in the same manner as in the synthesis of Intermediate I-9 (Yield: 62%). This compound was identified using LC-MS. $C_{29}H_{16}BrN_5$ calc.: 513.1. found [M+1] 514.1

Synthesis of Compound 65

2.16 g of Compound 65 was synthesized using Intermediate I-14 and 2-naphtalene boronic acid in the same manner as in the synthesis of Compound 3 (Yield: 77%). This compound was identified using HR-MS. $C_{39}H_{23}N_5$ calc.: 561.1953. found [M+1] 562.1953

$^1$H NMR (CDCl$_3$, 400 MHz) δ (ppm) 9.78-9.74 (m, 1H), 9.68 (s, 1H), 9.49 (s, 1H), 9.13 (s, 1H), 9.05-9.04 (m, 2H), 8.91-8.88 (m, 1H), 8.83-8.81 (m, 2H), 8.70-8.68 (d, 1H), 8.35-8.34 (m, 2H), 8.13 (s, 1H), 8.01-7.97 (t, 2H), 7.90-7.80 (m, 5H), 7.64-7.58 (dd, 2H), 7.53-7.49 (m, 11-1)

Example 1

To manufacture an anode, a coming 15 Ω/cm² (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 2-TNATA, which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 300 Å.

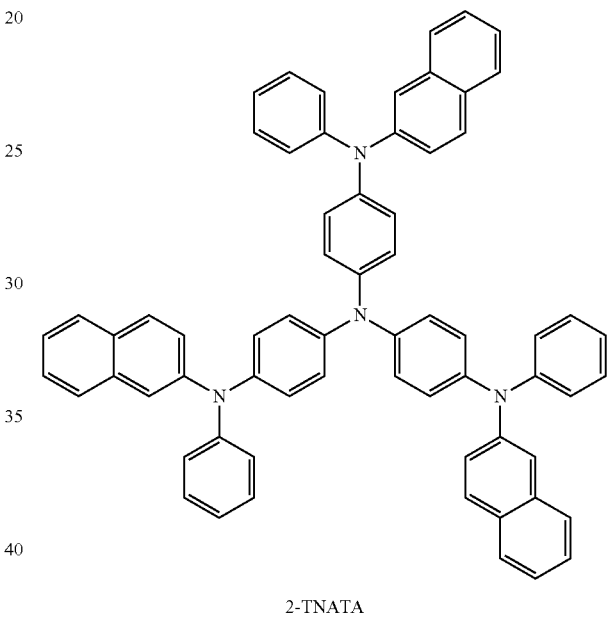

2-TNATA

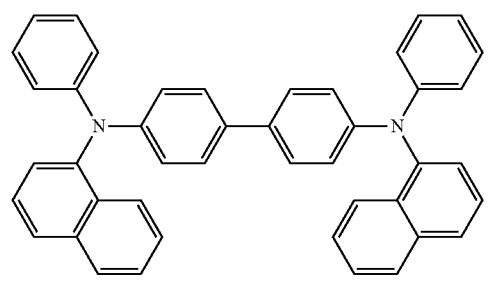

NPB

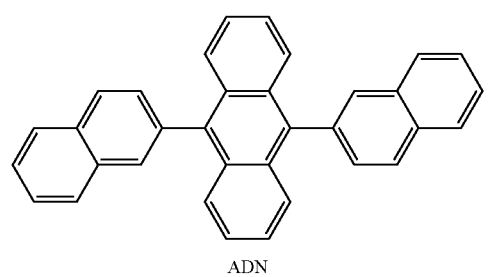

ADN

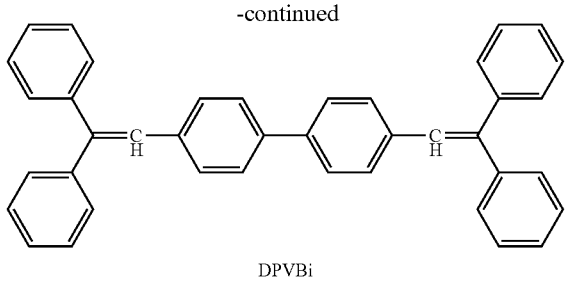

DPVBi

A blue fluorescent host 9,10-di-naphthalene-2-yl-anthracene (ADN) and a blue fluorescent dopant 1,4-bis-(2,2-diphenylvinyl)biphenyl (DPVBi), which are both widely known compounds, were deposited at the same time on the HTL in a weight ratio of 98:2 to form an EML having a thickness of 300 Å.

Then, Compound 3 was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3,000 Å, thereby forming an LiF/Al electrode and completing the manufacture of an organic light-emitting device.

The organic light-emitting device had a driving voltage of 6.20 V at a current density of 50 mA/cm$^2$, a high luminosity of 2187 cd/m$^2$, a luminescent efficiency of 4.37 cd/A, and a half-lifespan of 215 hours at 100 mA/cm$^2$.

Example 2

An organic light-emitting device was manufactured in the same manner as in Example 1, except that Compound 8 was used, instead of Compound 3, to form the ETL.

The organic light-emitting device had a driving voltage of 6.38 V at a current density of 50 mA/cm$^2$, a high luminosity of 2295 cd/m$^2$, a luminescent efficiency of 4.53 cd/A, and a half-lifespan of 226 hours at 100 mA/cm$^2$.

Example 3

An organic light-emitting device was manufactured in the same manner as in Example 1, except that Compound 18 was used, instead of Compound 3, to form the ETL.

The organic light-emitting device had a driving voltage of 6.46 V at a current density of 50 mA/cm$^2$, a high luminosity of 2005 cd/m$^2$, a luminescent efficiency of 4.67 cd/A, and a half-lifespan of 235 hours at 100 mA/cm$^2$.

Example 4

An organic light-emitting device was manufactured in the same manner as in Example 1, except that Compound 37 was used, instead of Compound 3, to form the ETL.

The organic light-emitting device had a driving voltage of 6.24 V at a current density of 50 mA/cm$^2$, a high luminosity of 2443 cd/d, a luminescent efficiency of 4.86 cd/A, and a half-lifespan of 221 hours at 100 mA/cm$^2$.

Example 5

An organic light-emitting device was manufactured in the same manner as in Example 1, except that Compound 53 was used, instead of Compound 3, to form the ETL.

The organic light-emitting device had a driving voltage of 6.18 V at a current density of 50 mA/cm$^2$, a high luminosity of 2758 cd/m$^2$, a luminescent efficiency of 5.51 cd/A, and a half-lifespan of 275 hours at 100 mA/cm$^2$.

Example 6

An organic light-emitting device was manufactured in the same manner as in Example 1, except that Compound 65 was used, instead of Compound 3, to form the ETL. The organic light-emitting device had a driving voltage of 6.45 V at a current density of 50 mA/cm$^2$, a high luminosity of 2682 cd/d, a luminescent efficiency of 5.36 cd/A, and a half-lifespan of 242 hours at 100 mA/cm$^2$.

Comparative Example 1

An organic light-emitting device was manufactured in the same manner as in Example 1, except that Alq3 was used, instead of Compound 3, to form the ETL.

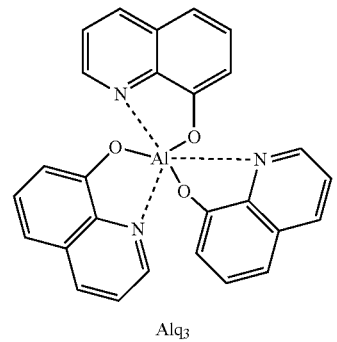

Alq$_3$

The organic light-emitting device had a driving voltage of 7.85 V at a current density of 50 mA/cm$^2$, a luminosity of 1560 cd/m$^2$, a luminescent efficiency of 3.12 cd/A, and a half-lifespan of 113 hours at 100 mA/cm$^2$.

When the heterocyclic compound of Formula 1 is used to form an electron transport layer of an organic light-emitting device, the driving voltage is lower by about 1V or greater as compared to when the widely-known material Alq3 is used, and good I-V-L characteristics with improved efficiency, and remarkable improvements in luminance and lifetime are attained.

The characteristics of the organic light-emitting devices of Examples 1-6 and Comparative Example 1 are shown in Table 1 below.

TABLE 1

| | ETL material | Driving voltage (V) | Current density (mA/cm$^2$) | Luminosity (cd/m$^2$) | Luminescent efficiency (cd/A) | Emission color | Half life-span (hr @100 mA/cm$^2$) |
|---|---|---|---|---|---|---|---|
| Example 1 | Compound 3 | 6.20 | 50 | 2,008 | 4.01 | blue | 207 hr |
| Example 2 | Compound 8 | 6.38 | 50 | 2,295 | 4.53 | blue | 226 hr |
| Example 3 | Compound 18 | 6.46 | 50 | 2,005 | 4.67 | blue | 235 hr |

TABLE 1-continued

|  | ETL material | Driving voltage (V) | Current density (mA/cm$^2$) | Luminosity (cd/m$^2$) | Luminescent efficiency (cd/A) | Emission color | Half life-span (hr @100 mA/cm$^2$) |
|---|---|---|---|---|---|---|---|
| Example 4 | Compound 37 | 6.24 | 50 | 2,443 | 4.89 | blue | 221 hr |
| Example 5 | Compound 53 | 6.18 | 50 | 2,758 | 5.51 | blue | 275 hr |
| Example 6 | Compound 65 | 6.45 | 50 | 2,682 | 5.36 | blue | 242 hr |
| Comparative Example 1 | Alq3 | 7.85 | 50 | 1,560 | 3.12 | blue | 113 hr |

As described above, novel heterocyclic compounds according to the one or more of the above embodiments of the present invention have good emission characteristics and charge transporting capabilities, and thus may be used as an electron injecting/transporting material for most color-fluorescent and phosphorescent devices, such as red, green, blue, and white fluorescent and phosphorescent devices, and in particular as a light-emitting material of green, blue, or white fluorescent device. Thus, an organic light-emitting device with high-efficiency, low-driving voltage, high luminance and long lifespan may be manufactured using the heterocyclic compounds.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 1 below:

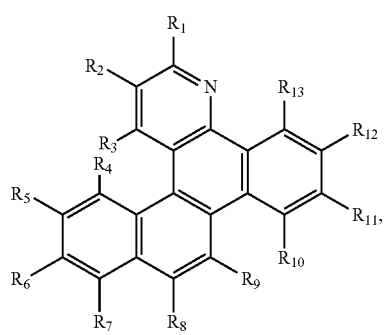

[Formula 1]

$R_1$ to $R_{13}$ in Formula 1 are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ aryl group, an amino group substituted with a $C_6$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group, where $R_1$ to $R_{13}$ are not all hydrogen atoms and $R_8$ is not a halogen atom when $R_1$-$R_7$ and $R_9$-$R_{13}$ are all hydrogen atoms; and $R_1$ and $R_2$ are optionally linked to form an aromatic ring.

2. The heterocyclic compound of claim 1, wherein $R_1$, $R_2$, and $R_8$ in Formula 1 are each independently a substituted or unsubstituted $C_6$-$C_{20}$ aryl group, a substituted or unsubstituted $C_3$-$C_{20}$ heteroaryl group, or a substituted or unsubstituted $C_5$-$C_{20}$ condensed polycyclic group.

3. The heterocyclic compound of claim 1, wherein $R_3$ to $R_7$, and $R_9$ to $R_{13}$ in Formula 1 are each independently a hydrogen atom or a deuterium atom.

4. The heterocyclic compound of claim 1, $R_1$ and $R_2$ in Formula 1 each being independently selected from the group consisting of a hydrogen atom, a deuterium atom, a halogen atom, a cyano group, a substituted or unsubstituted $C_1$-$C_{20}$ alkyl group, and groups represented by Formulae 2a to 2e below:

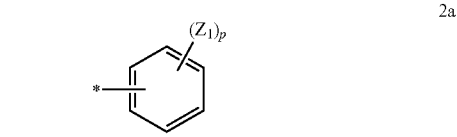

2a

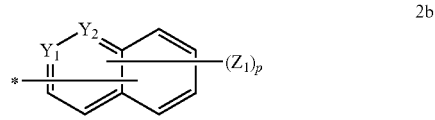

2b

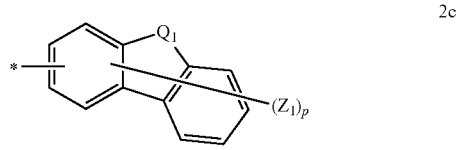

2c

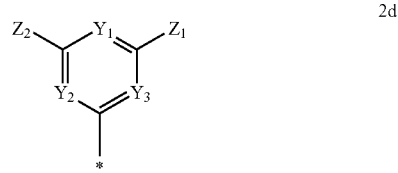

2d

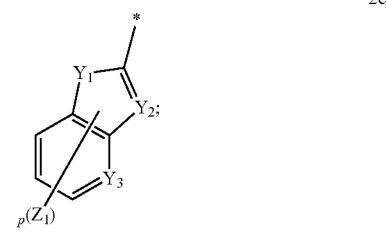

2e $Q_1$ in Formulae 2a to 2e is a linking group represented by —C($R_{14}$)($R_{15}$)—, —N($R_{16}$)—, —S—, or —O—;

$Y_1$, $Y_2$, and $Y_3$ are each independently a linking group represented by —N═, —N($R_{17}$)—, or —C($R_{18}$)═;

$Z_1$, $Z_2$, $R_{14}$, $R_{15}$, $R_{16}$, $R_{17}$, and $R_{18}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 7; and

* indicates a binding site.

5. The heterocyclic compound of claim 1, $R_8$ in Formula 1 being one of the groups represented by Formulae 3a to 3j below:

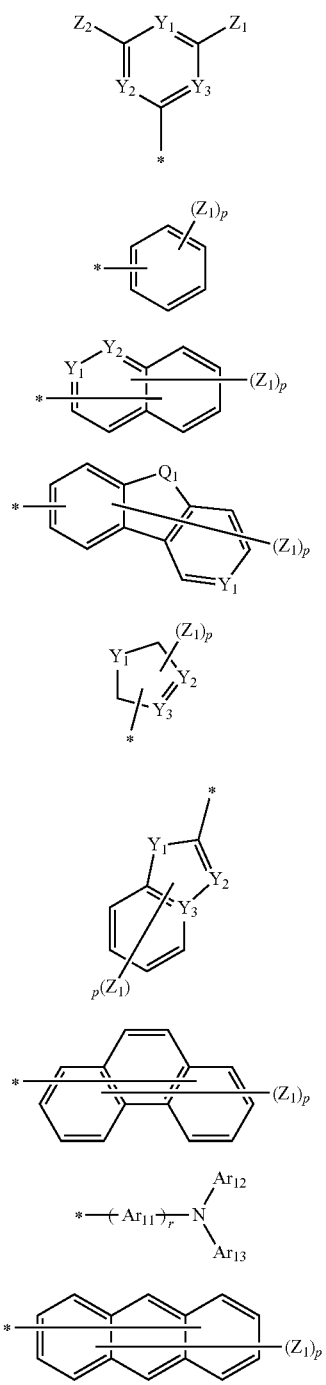

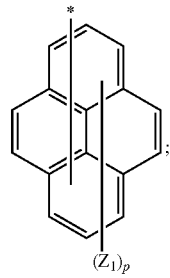

$Q_1$ in Formulae 3a to 3j is a linking group represented by —$C(R_{14})(R_{15})$—, —$N(R_{16})$—, —S—, or —O—;

$Y_1$, $Y_2$, and $Y_3$ are each independently a linking group represented by —O—, —N═, —$N(R_{17})$—, or —$C(R_{18})$═;

$Z_1$, $Z_2$, $Ar_{12}$, $Ar_{13}$, $R_{14}$, $R_{15}$, $R_{16}$, $R_{17}$, and $R_{18}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

$A_{11}$ is a substituted or unsubstituted $C_1$-$C_{20}$ alkylene group, a substituted or unsubstituted $C_6$-$C_{20}$ arylene group, or a substituted or unsubstituted $C_3$-$C_{20}$ heteroarylene group;

p is an integer from 1 to 9;

r is an integer from 0 to 5; and

* indicates a binding site.

6. The heterocyclic compound of claim 1, $R_1$ and $R_2$ in Formula 1 each being independently selected from the group consisting of a hydrogen atom, a deuterium atom, and groups represented by Formulae 4a to 4g below, or are linked to form a benzene ring:

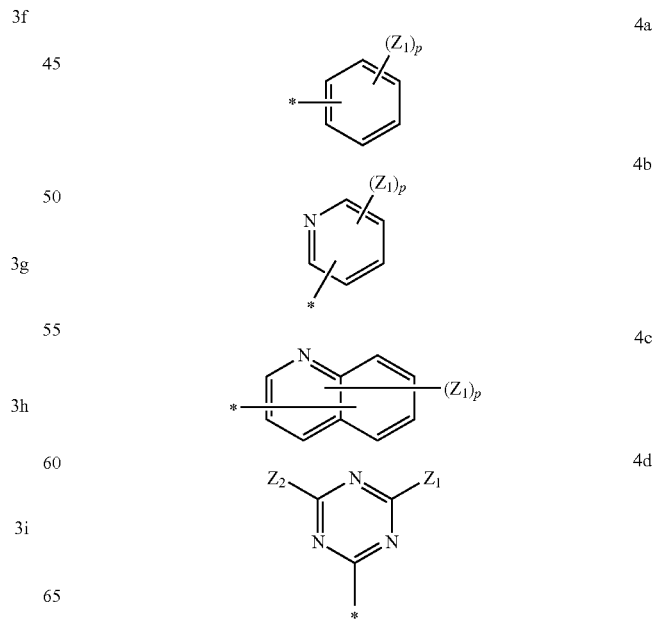

-continued

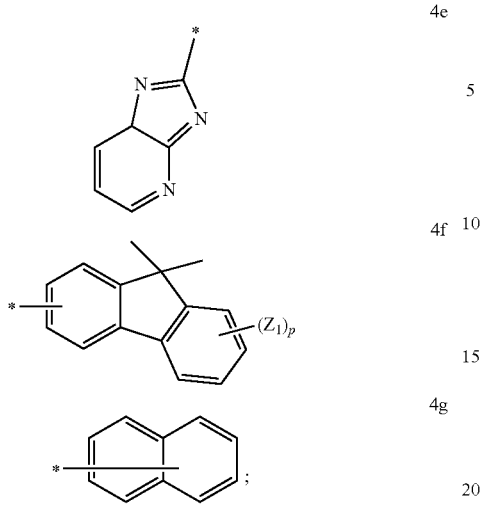

$Z_1$ and $Z_2$ in Formulae 4a to 4g are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;
p is an integer from 1 to 6; and
* indicates a binding site.

7. The heterocyclic compound of claim 1, $R_8$ in Formula 1 being one of the groups represented by Formulae 5a to 5o below:

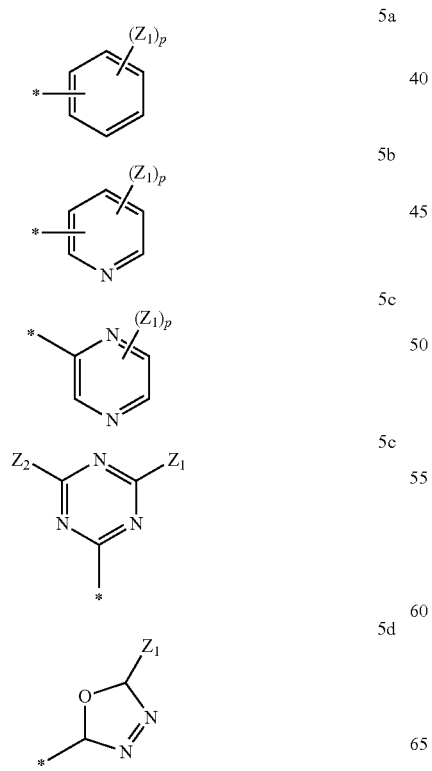

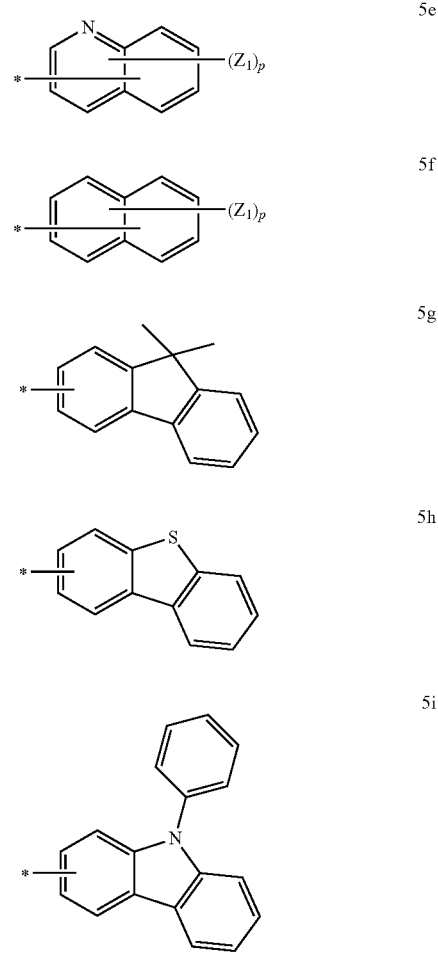

73
-continued

5m

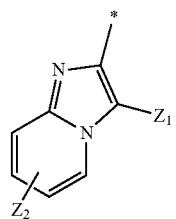

5n

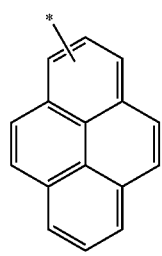

5o

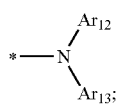

$Z_1$, $Z_2$, $Ar_{12}$, and $Ar_{13}$ in Formulae 5a to 5o are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 7; and

* indicates a binding site.

8. The heterocyclic compound of claim 1, the compound of Formula 1 comprising one of the compounds below:

3

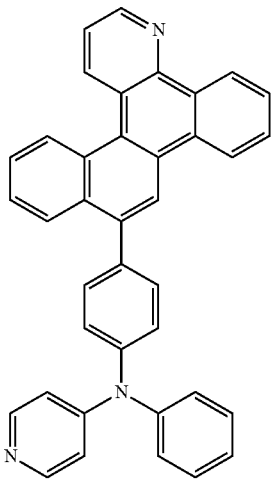

74
-continued

8

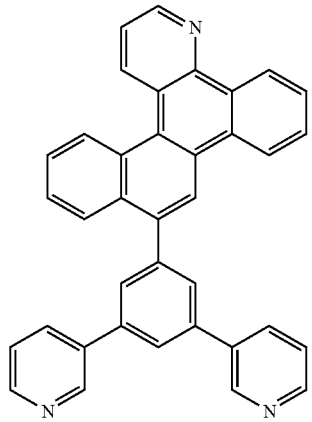

18

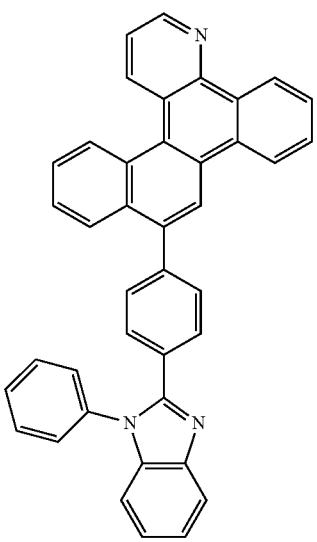

37

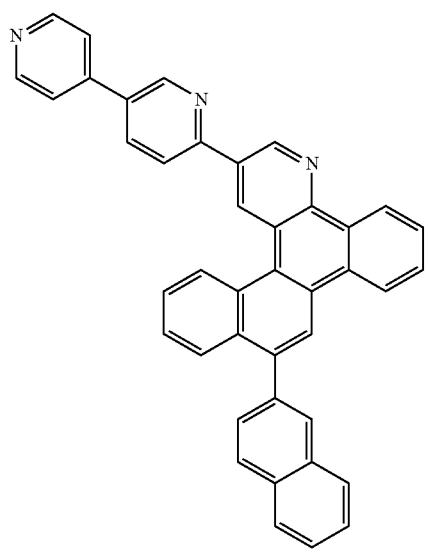

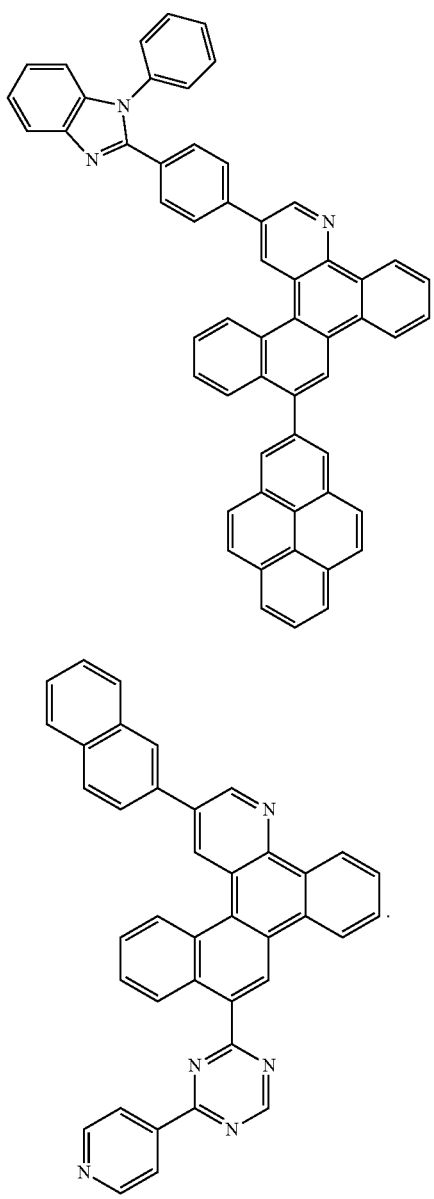

9. An organic light-emitting device comprising:
a first electrode;
a second electrode; and
an organic layer between the first electrode and the second electrode, the organic layer comprising a first layer including the heterocyclic compound of claim 1.

10. The organic light-emitting device of claim 9, wherein the first layer comprises at least one layer selected from the group consisting of a hole injection layer, a hole transport layer, a functional layer having both hole injection and hole transport capabilities, an emission layer, an electron injection layer, an electron transport layer, and a functional layer having both electron injection and electron transport capabilities.

11. The organic light-emitting device of claim 9, wherein the first layer comprises at least one layer selected from the group consisting of a hole injection layer, a hole transport layer, a functional layer having both hole injection and hole transport capabilities, an emission layer, an electron injection layer, an electron transport layer, and a functional layer having both electron injection and electron transport capabilities, and the first layer further comprises a charge generating material.

12. The organic light-emitting device of claim 9, wherein the organic layer further comprises a hole injection layer, a hole transport layer, a functional layer having both hole injection and hole transport capabilities, an emission layer, a hole blocking layer, an electron transport layer, an electron injection layer, or a combination of at least two thereof.

13. The organic light-emitting device of claim 12, wherein at least one of the hole injection layer, the hole transport layer, and the functional layer having hole injection and hole transport capabilities further comprises a charge generating material.

14. The organic light-emitting device of claim 12, wherein the emission layer comprises a host and a dopant, the dopant comprising a fluorescent dopant or a phosphorescent dopant.

15. The organic light-emitting device of claim 14, wherein the phosphorescent dopant comprises an organometallic complex including at least one selected from the group consisting of iridium (Ir), platinum (Pt), osmium (Os), rhenium (Re), titanium (Ti), zirconium (Zr), hafnium (Hf), and a combination of at least two thereof.

16. The organic light-emitting device of claim 12, wherein the electron transport layer comprises an electron transporting organic material and a metal-containing material.

17. The organic light-emitting device of claim 16, wherein the metal-containing material comprises a lithium (Li) complex.

18. The organic light-emitting device of claim 9, wherein the first layer comprising the heterocyclic compound of Formula 1 of claim 1 is formed using a wet process.

19. A flat panel display device comprising the organic light-emitting device of claim 9, wherein the first electrode of the organic light-emitting device is electrically connected to a source electrode or a drain electrode of a thin-film transistor.

* * * * *